(12) United States Patent
Kanellos et al.

(10) Patent No.: US 6,960,463 B2
(45) Date of Patent: Nov. 1, 2005

(54) SEPARATION OF FIBRINOGEN FROM PLASMA PROTEASES

(75) Inventors: Jerry Kanellos, Clifton Hill (AU); Michael Kleinig, Brunswick (AU); Teresa Martinelli, Thornbury (AU)

(73) Assignee: CSL Limited, Victoria (AU)

( * ) Notice: Subject to any disclaimer, the term of this patent is extended or adjusted under 35 U.S.C. 154(b) by 143 days.

(21) Appl. No.: 10/168,800

(22) PCT Filed: Dec. 21, 2000

(86) PCT No.: PCT/AU00/01585

§ 371 (c)(1),
(2), (4) Date: Aug. 30, 2002

(87) PCT Pub. No.: WO01/48016

PCT Pub. Date: Jul. 5, 2001

(65) Prior Publication Data

US 2003/0211591 A1 Nov. 13, 2003

(30) Foreign Application Priority Data

Dec. 23, 1999 (AU) ............................................. PQ4841
Dec. 23, 1999 (AU) ............................................. PQ4842

(51) Int. Cl.$^7$ ............................ C12N 9/64; C07K 14/75
(52) U.S. Cl. ....................................... 435/226; 530/382
(58) Field of Search .................... 435/7, 226; 530/350, 530/382, 383; 514/8, 12, 21

(56) References Cited

U.S. PATENT DOCUMENTS

| 4,341,764 A | | 7/1982 | Wallace et al. |
| 4,362,567 A | | 12/1982 | Schwartz et al. |
| 4,377,572 A | | 3/1983 | Schwarz et al. |
| 4,650,678 A | | 3/1987 | Fuhge et al. |
| 4,789,733 A | * | 12/1988 | Winkelman ................. 530/383 |
| 4,960,757 A | | 10/1990 | Kumpe et al. |
| 5,484,890 A | * | 1/1996 | Johnson et al. .............. 530/383 |
| 5,605,887 A | * | 2/1997 | Pines et al. .................... 514/21 |
| 5,834,420 A | | 11/1998 | Laub et al. |
| 6,277,961 B1 | | 8/2001 | Hock et al. |

FOREIGN PATENT DOCUMENTS

| EP | 0748 337 B1 | 6/1999 |
| GB | 2 102 811 A | 2/1983 |
| WO | WO 9/23111 | 5/1999 |
| WO | WO 99/37680 | 7/1999 |

OTHER PUBLICATIONS

Smith RT, Von Korff RW. A heparin–precipitable fraction of human plasma. I. Isolation and characterization of the fraction Clin Invest. Apr. 1957;(44):596–604.*
Tien SL, Ong YW, Lim SH, Chiang T. Yields of fibronectin by heparin–cold–precipitation from plasma. Ann Acad Med Singapore Nov. 1990;19(6):831–2.*
Palmer DS, Ganz PR, Perkins H, Rosborough D, Rock G. Development of a heat–treated factor VII/von Willebrand factor concentrate prepared from heparinized plasma.Thromb Haemost. Jun. 28, 1990;63(3):392–402.*
Tien, S.L., et al "Yields of Fibronectin by Heparin–Cold–Precipitation from Plasma"; *Anals Academy of Medicine*; vol. 19, No. 6, pp. 831–832 (1990).
Palmer, D.S., et al; "Development of a Heat–Treated factor VIII/von Willebrand Factor Concentrate Prepared from Heparinized Plasma"; *PubMed Medline Query; Thromb Haemost*, Jun. 28, 1990; 63(3):392–402.

* cited by examiner

*Primary Examiner*—Jon Weber
*Assistant Examiner*—Sheridan Snedden
(74) *Attorney, Agent, or Firm*—Nixon & Vanderhye

(57) ABSTRACT

The present invention relates to methods for purifying fibrinogen. In one aspect, the present invention relates to a method of separating fibrinogen from plasma fraction I precipitate. In another aspect, the invention relates to the purification of fibrinogen using ion exchange chromatography.

46 Claims, 6 Drawing Sheets

SEPARATION OF FIBRINOGEN FROM PLASMA PROTEASES

This application is a 371 of PCT/AU00/01585 and claims foreign priority to Australian application PQ 4842, filed 23 Dec. 1999, and Australian application PQ 4841, filed filed 23 Dec. 1999.

FIELD OF THE INVENTION

The present invention relates to methods for purifying fibrinogen. In one aspect, the present invention relates to a method of separating fibrinogen from plasma fraction I precipitate. In another aspect, the invention relates to the purification of fibrinogen using ion exchange chromatography.

BACKGROUND OF THE INVENTION

The isolation of human fibrinogen has traditionally been carried out by classical plasma fractionation methods. Fibrinogen is precipitated from plasma either with ethanol (Blomback and Blomback, 1956), ammonium sulphate (Takeda, 1996), β alanine/glycine (Jakobsen and Kieruif, 1976), polymers (polyethelene glycol) and low ionic strength solutions (Holm, 1985) with relative high yield and homogeneity.

Further purification of fibrinogen precipitates can be achieved by ion-exchange chromatography conditions (Stathakis et al, 1978) and affinity chromatography (Kuyas et al, 1990). Specific contaminants can be absorbed out for example fibronectin on immobilised gelatine and plasminogen an immobilised lysine (Vuento et al, 1979).

Precipitation methods are widely used for the manufacture of commercial fibrinogen. Chromatographic methods are now being explored as an alternative or to improve the purity of fibrinogen concentrates.

WO 99/37680 describes a method for the large scale separation of fibrinogen from other blood proteins in human blood plasma. The process involves the use of a heparin precipitated paste as a starting material for the purification of fibrinogen. The heparin precipitated paste is a by-product from the manufacturing process of Factor VIII (Antihaemophilic Factor, AHF).

Attempts to produce fibrinogen free of plasminogen or to purify plasminogen itself have been widely published in the literature. The most common method is to utilise the ability of lysine to bind to one of the two "kringles" in the plasminogen molecule. The use of affinity chromatography step was first disclosed in a paper published by Deutsch and Mertz in 1970. Baxter International Inc. utilised this technology, which incorporated the use of lysine-sepharose material in a dedicated step to remove plasminogen from their fibrinogen as disclosed in the patent WO 95/25748 for the large scale manufacture of a fibrinogen concentrate free of destabilising levels of plasminogen product. Other techniques published in the scientific literature again utilise the binding of either lysine or $\epsilon$-amino caproic acid. However, they are employed to alter the solubility of the plasminogen molecule. Following the addition of lysine to a dilute fibrinogen solution, the subsequent solution is then precipitated in the presence of 7% ethanol. Removal of plasminogen is stated at greater than 90% with a repeat of the step leading to total removal of the contaminant (Mosesson, 1962). Precipitation methods are widely used for the manufacture of commercial fibrinogen, however, the work published by Mosesson (1962) relys on a dilute solution of fibrinogen which is not a practical process for implementation at a production scale.

The use of ion-exchange chromatography and $\epsilon$-amino caproic acid to bind and elute plasminogen independent of pH or ionic strength was disclosed in a patent (WO 94/00483) lodged in 1994 by Novo Nordisk A/S describing the purification of kringle containing proteins. This method chooses S-sepharose as the resin of choice. Also, a combination of gel filtration and ion-exchange chromatography has been utilised to purify plasminogen. (Robbins et al, 1965).

SUMMARY OF THE INVENTION

The present inventors have now found that fibrinogen may be recovered in a purified form from a starting material consisting of Fraction I paste. The fibrinogen recovered in this process is free of destabilising levels of plasminogen and other proteases. Fibrinogen recovered in this manner also contains factor XIII, which is required to enhance the cross-linking of fibrin polymers in the production of fibrin glue. Furthermore, the yields of fibrinogen obtained by this process are unexpectedly higher than those obtained in methods which use alternative starting materials, such as heparin precipitated paste.

The present inventors have also developed an improved method for recovering fibrinogen from an ion-exchange column which involves the addition of at least one ω-amino acid to the fibrinogen-containing material applied to the column or to the solution used to wash the column prior to elution of the fibrinogen.

When used herein, the phrase "Fraction I precipitate" refers to frozen plasma which has been thawed and the cryoprecipitate removed by centrifugation. The resultant cryosupernatant is then mixed with ethanol to precipitate Fraction I.

Accordingly, in a first aspect the present invention provides a method of purifying fibrinogen, which method comprises extracting fibrinogen from a Fraction I precipitate by admixing the Fraction I precipitate with an extraction buffer such that fibrinogen is solubilised in the extraction buffer, wherein the extraction buffer comprises salt at a concentration of at least 0.1M and heparin at a concentration of at least 10 IU/ml.

In a preferred embodiment of the first aspect, the concentration of salt is at least 0.2M, more preferably at least 0.4M, more preferably about 0.8M.

In a further preferred embodiment of the first aspect, the extraction buffer comprises at least one salt selected from the group consisting of chloride, phosphate and acetate salts, and more preferably comprises NaCl.

In a further preferred embodiment of the first aspect, the extraction buffer also comprises Tri-sodium citrate at a concentration of about 20 mM.

In a further preferred embodiment of the first aspect, the extraction buffer further comprises at least one ω-amino acid. Preferably, the at least one ω-amino acid is present in the extraction buffer at a concentration of at least 5 mM.

In a further preferred embodiment of the first aspect, the extraction buffer comprises antithrombin III (ATIII) at a concentration of at least about 1 IU/ml.

In a further preferred embodiment of the first aspect, the extraction buffer comprises Tri-sodium citrate at a concentration of about 20 mM, NaCl at a concentration of about 0.8M, heparin at a concentration of about 60 IU/ml and at least one ω-amino acid at a concentration of about 5 mM. Preferably the extraction buffer has a pH of about 7.3.

In a further preferred embodiment of the first aspect, the extraction of fibrinogen is performed at about 37° C.

Preferably, the extraction is performed for at least 60, more preferably at least 90 minutes.

In a further preferred embodiment of the first aspect, the method further comprises the step of incubating the extracted fibrinogen solution with aluminium hydroxide followed by centrifugation and removal of the precipitate.

In a further preferred embodiment of the first aspect, the method further comprises the step of precipitating the fibrinogen from the extracted fibrinogen solution by the addition of a glycine saline. (Gly/NaCl) buffer. Preferably, the Gly/NaCl buffer comprises glycine at a concentration of around 2.1M, Na-citrate at a concentration of around 20 mM, sodium chloride at a concentration of around 3.6M and $CaCl_2$ at a concentration of around 2.4 mM.

In a further preferred embodiment of the first aspect, the method further comprises the step of resolubilising the fibrinogen precipitate in a buffer comprising NaCl at a concentration of around 100 mM, $CaCl_2$ at a concentration of around 1.1M, Na-citrate at a concentration of around 10 mM, tris at a concentration of around 10 mM and sucrose at a concentration of around 45 mM, preferably with a pH of about 6.9.

In a further preferred embodiment of the first aspect, the method further comprises the steps of:

applying the extracted fibrinogen solution to an ion exchange matrix under conditions such that fibrinogen binds to the matrix;

eluting the fibrinogen from the matrix; and optionally recovering the fibrinogen from the eluate.

In a further preferred embodiment of the first aspect, the method further comprises washing the ion exchange matrix with a buffer comprising at least one ω-amino acid prior to eluting the fibrinogen from the matrix. Preferably the wash buffer comprises the at least one ω-amino acid at a concentration of at least 5 mM.

In a further preferred embodiment, the wash buffer comprises (i) tris at a concentration of about 50 mM, (ii) at least one ω-amino acid at a concentration of about 20 mM, and NaCl at a concentration of about 90 mM. Preferably, the buffer has a pH of about 8.0. Preferably, the buffer has a conductivity of about 11.1 mS/cm.

In a second aspect, the present invention provides a method of purifying fibrinogen, which method comprises:

(a) extracting fibrinogen from a Fraction I precipitate by admixing the Fraction I precipitate with an extraction buffer such that fibrinogen is solubilised in the extraction buffer, wherein the extraction buffer comprises salt at a concentration of at least 0.1M;

(b) precipitating the fibrinogen; and (c) solubilising the fibrinogen in a solution comprising at least one ω-amino acid at a concentration of at least 100 mM.

In a preferred embodiment of the second aspect, the concentration of salt in the extraction buffer is at least 0.2M, more preferably at least 0.4M, more preferably about 0.8M.

In a further preferred embodiment of the second aspect, the extraction buffer comprises at least one salt selected from the group consisting of chloride, phosphate and acetate salts, and more preferably comprises NaCl.

Preferably, the extraction buffer also comprises Tri-sodium citrate at a concentration of about 20 mM.

In a preferred embodiment of the second aspect, the extraction buffer further comprises heparin at a concentration of at least 10 IU/ml, more preferably about 60 IU/ml.

In a further preferred embodiment of the second aspect, the extraction buffer further comprises at least one ω-amino acid. Preferably, the at least one ω-amino acid is present in the extraction buffer at a concentration of at least 5 mM.

In a further preferred embodiment of the second aspect, the extraction buffer comprises Na-citrate at a concentration of about 20 mM, NaCl at a concentration of about 0.8M and heparin at a concentration of about 60 IU/ml. Preferably the extraction buffer has a pH of about 7.3.

In a further preferred embodiment of the second aspect, the fibrinogen is precipitated in step (b) by the addition of a glycine saline (Gly/NaCl) buffer. Preferably, the Gly/NaCl buffer comprises glycine at a concentration of around 2.1M, Na-citrate at a concentration of around 20 mM, sodium chloride at a concentration of around 3.6M and $CaCl_2$ at a concentration of around 2.4 mM.

In a further preferred embodiment of the second aspect, the fibrinogen precipitate is solubilised in step (c) using a buffer comprising NaCl at a concentration of around 100 mM, $CaCl_2$ at a concentration of around 1.1M, Na-citrate at a concentration of around 10 mM, tris at a concentration of around 10 mM and sucrose at a concentration of around 45 mM. Preferably, the buffer has a pH of about 6.9.

In a further preferred embodiment of the second aspect, the method further comprises:

(d) applying the fibrinogen solution from step (c) to an ion exchange matrix under conditions such that fibrinogen binds to the matrix;

(e) eluting the fibrinogen from the matrix; and (f) optionally recovering the fibrinogen from the eluate.

In a preferred embodiment of the second aspect, the method further comprises washing the ion exchange matrix with a buffer comprising at least one ω-amino acid prior to eluting the fibrinogen from the matrix. Preferably the wash buffer comprises the at least one ω-amino acid at a concentration of at least 5 mM.

In a further preferred embodiment of the second aspect, the wash buffer comprises (i) tris at a concentration of about 50 mM, (ii) at least one ω-amino acid at a concentration of about 20 mM, and NaCl at a concentration of about 90 mM. Preferably, the buffer has a pH of about 8.0. Preferably, the buffer has a conductivity of about 11.1 mS/cm.

In a further preferred embodiment of the second aspect, the fibrinogen containing solution (preferably comprising the ω-amino acid) is diluted such that the conductivity is below 10.5 mS/cm before it is applied to the ion exchange matrix.

In a further preferred embodiment of the second aspect, the fibrinogen is eluted from the matrix in a buffer comprising about 10 mM Tris, 10 mM citrate, 45 mM sucrose; and NaCl at a concentration of between 200 mM to 1.0M, more preferably about 400 mM. Preferably, the buffer has a pH of about 7.0.

In a third aspect the present invention provides a method of purifying fibrinogen, which method comprises:

(a) extracting fibrinogen from a fibrinogen containing material by admixing the material with an extraction buffer such that fibrinogen is solubilised in the extraction buffer, wherein the extraction buffer comprises at least one ω-amino acid at a concentration of at least 5 mM;

(b) applying the extraction buffer from step (a) to an ion exchange matrix under conditions such that fibrinogen binds to the matrix;

(c) eluting the fibrinogen from the matrix; and (d) optionally recovering the fibrinogen from the eluate.

In a preferred embodiment of the third aspect, the method further comprises washing the ion exchange matrix after step (b) with a solution comprising at least one ω-amino acid.

In a fourth aspect the present invention provides a method of purifying fibrinogen from a fibrinogen containing solution which method comprises:

(a) applying the solution to an ion exchange matrix, under conditions such that fibrinogen binds to the matrix;

(b) washing the ion exchange matrix with a solution comprising at least one ω-amino acid;

(c) eluting the fibrinogen from the matrix; and (d) optionally recovering the fibrinogen from the eluate.

In a preferred embodiment of the fourth aspect, the method further comprises adding at least one ω-amino acid to the solution before applying to the ion exchange matrix.

In the context of the third and fourth aspects of the present invention, the fibrinogen containing material may be any material derived from plasma which includes fibrinogen. Examples of such solutions include, but are not limited to, plasma (including anti-coagulated plasma), or plasma fractions. In preferred embodiment, the material is a heparin precipitated paste, which is a by-product in the manufacturing process of Factor VIII. The heparin precipitated paste may be solubilised with a salt solution to provide a fibrinogen preparation of high specific activity. A process for precipitating fibrinogen from a cryoprecipitate extract using heparin as described in Winkelman et al. 1989, the entire contents of which are incorporated herein by reference. Alternatively, the fibrinogen containing material is extracted from Fraction 1 precipitate, preferably in accordance with a method of the first or second aspects of the present invention.

In a further preferred embodiment of the third or fourth aspects, the ω-amino acid is present in the extraction buffer at a concentration of between 5–500 mM, more preferably between 50–500 mM, and more preferably around 100 mM.

In a further preferred embodiment of the third or fourth aspects, the fibrinogen containing solution (preferably comprising the ω-amino acid) is diluted such that the conductivity is below 10.5 mS/cm before it is applied to the ion exchange matrix.

In a further preferred embodiment of the third or fourth aspects, the buffer used to wash the ion exchange matrix comprises (i) tris at a concentration of about 50 mM, (ii) a ω-amino acid at a concentration of about 20 mM, and NaCl at a concentration of about 90 mM. Preferably, the buffer has a pH of about 8.0. Preferably, the buffer has a conductivity of about 11.1 mS/cm.

In a further preferred embodiment of the third or fourth aspects, the fibrinogen is eluted from the matrix in a buffer comprising about 10 mM Tris, 10 mM citrate, 45 mM sucrose; and NaCl at a concentration of between 200 mM to 1.0M, more preferably about 400–500 mM. Preferably, the buffer has a pH of about 7.0.

In a preferred embodiment of the first, second, third or fourth aspects of the present invention, the ω-amino acid contains at least 4 carbon atoms in the carbon chain between the carboxylic acid and the ω-amino group. The carbon chain may be linear or cyclic. Examples of suitable linear ω-amino acids are 4-aminobutyric acid, 5-aminopentoic acid, 6-aminohexanoic acid (ε-amino caproic acid (EACA)), 7-aminoheptanoic acid, 8-aminooctanoic acid, and arginine. Examples of cyclic ω-amino acids are trans-4-aminomethyl cyclohexane carboxylic acid (tranexamic acid) and para-aminomethyl benzoic acids. In a particularly preferred embodiment, the ω-amino acid is EACA.

Ion exchange matrices are known in the art and any suitable matrix may be used in the present invention. A preferred matrix is the MacroPrep HQ Resin (BioRad, catalaogue no. 156-0041). In a further preferred embodiment, the ion exchange matrix is loaded into a column.

It will be appreciated by those skilled in the art that the methods of the third and fourth aspects have the potential to provide an alternative to affinity chromatography for the large scale production of fibrinogen free of destabilising levels of plasminogen and other proteases. The methods in these aspects require only a single processing step using ion exchange chromatography for the isolation of fibrinogen free of destabilising levels of plasminogen and other proteases from biological fluids with a high recovery rate (approximately 75%). The use of this novel method for the purification of fibrinogen from blood proteins has the potential to enable a simpler method of manufacture leading to a product which is superior in both purity and stability.

The technology of the current invention offers many advantages with regards to both the manufacture of fibrinogen and the use of fibrinogen in a fibrin sealant product. The removal of plasminogen from the fibrinogen component allows the manufacturer the liberty of not having to add inhibitory agents, either human, animal or synthetically derived, in order to obtain the desired stability of the fibrinogen component and fibrin glue. Addition of inhibitory agents can lend itself to other problems which are avoided by the removing plasminogen from the final product.

Finally, the production costs of an ion-exchange resin is far more economical than the cost of lysine-sepharose or immobilised lysine resin which are used in affinity chromatography procedures.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

| Abbreviations used herein: | |
|---|---|
| TP | Total Protein |
| CP | Clottable protein |
| FXIII | Factor XIII |
| FII | Factor II |
| Plasm. | Plasminogen |
| FN | Fibronectin |
| ATIII | Antithrombin III |
| F1P | Fraction 1 paste |
| SFP | Solubilised fraction 1 paste |
| ASFP | Alhydrogel absorbed solubilised fraction 1 paste |
| GASFP | Resolubilised Gly/NaCl precipitated solubilised fraction 1 paste |
| SDS-PAGE | Sodium dodecyl sulphate-polyacrylamide gel electrophoresis |
| Gly/NaCl | Glycine/Saline |
| SD | Solvent/detergent |
| εACA | epsilon aminocaproic acid |
| TNBP | Tri-N-butyl phosphate |
| Al(OH)$_3$ | Aluminium hydroxide |
| RT | Room temperature |
| PET | Plasma Engineering Technology |
| IEX | Ion exchange |
| SHP | Solubilised heparin paste supernatant |

DETAILED DESCRIPTION OF THE PREFERRED EMBODIMENTS

EXAMPLE 1

Figure 1:
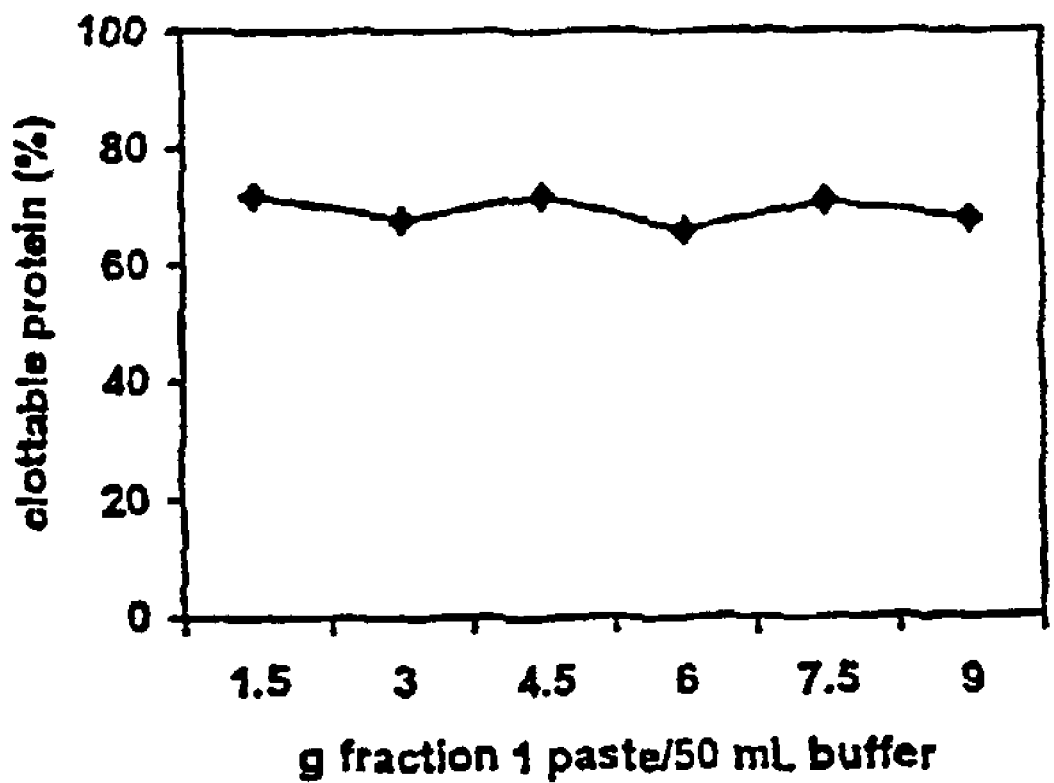
FIG. 1: Yield of clottable fibrinogen obtained in paste to buffer ratio study (I)

Extraction of Fibrinogen from Fraction 1 Precipitate 1.1 Materials and Methods
1.1.1 Heparin Paste Extraction Procedure Fraction I paste is extracted at a ratio of 1 g:8.33 g heparin paste extraction buffer unless stated otherwise. The extraction is performed at room temperature for 2 hours.

1.1.2 Heparin Paste Extraction Buffer
0.4 M NaCl,
5 mM εACA,
20 mM Na-citrate,
pH 7.3.

1.1.3 Alhydrogel Absorption

A solution of 2% aluminium hydroxide $Al(OH)_3$, also known as alhydrogel, is added to solubilised heparin paste superntant (SHP) at a concentration of 10.8%. The mixture is incubated with stirring for 15 minutes at room temperature, centrifuged for 10 minutes, and the pellet discarded.

1.1.4 Gly/NaCl Precipitation

The alhydrogel supernatant (ASFP) and Gly/NaCl buffer are heated to 30° C.±3° C. The supernatant is then added to the Gly/NaCl buffer, over 4.5 minutes, at a ratio of 1:2.05. The supernatant is then incubated at 30° C. with stirring for 20 mins, before centrifuging for 10 mins at 5010 g. The supernatant is discarded and the precipitate resolubilised using a volume of Buffer D equal to one third of the mass of the supernatant obtained after extraction of fibrinogen from Fraction I paste. The precipitate may be stirred at room temperature during resolubilisation.

1.1.5 Gly/NaCl Buffer
2.1M glycine
20 mM Na-citrate
3.6M NaCl
2.4 mM $CaCl_2$ 1.1.6 Buffer D
100 mM NaCl
1.1 mM $CaCl_2$
10 mM Na-citrate
10 mM tris
45 mM sucrose
pH 6.9

1.1.7 Solvent Detergent Treatment

Solvent detergent treatment is performed by adding 1% polysorbate 80 and 0.3% TNBP to the resolubilised Gly/NaCl precipitate (GASFP).

1.1.8 Wet Heat Treatment

Solvent detergent treated fibrinogen is diluted 1/15 with concentrated sucrose/glycine buffer to a final concentration of approximately 1 mg/mL protein, 60% sucrose and 1 M glycine. The formulated product is heated to 60° C. and incubated for 10 hours.

1.1.9 Ion Exchange Chromatography

Wet heat treated fibrinogen is applied to an equilibrated anion exchange resin. After washing of the resin, the product is eluted using a salt-containing buffer.

1.1.10 Stability at 37° C.

In process samples were incubated at 37° C. in a water bath and samples taken and frozen at regular time intervals. The stability samples were analysed by SDS-PAGE under reducing conditions. Stability was assessed qualitatively as the last time point where no degradation of the α subunit of fibrinogen was observable by eye on the gel.

1.1.11 Extraction 1 Procedure

Fraction 1 paste was obtained fresh from production. 6 g was extracted immediately using heparin paste extraction buffer. The solubilised fraction 1 paste was then aliquoted and stored frozen at −80° C. until assayed.

1.1.12 Extraction 2 Procedure

Fraction 1 paste was obtained fresh from production. 12 g was extracted immediately using heparin paste extraction buffer. The paste was treated with $Al(OH)_3$ and then precipitated using Gly/NaCl buffer. The precipitate was resolubilised in Buffer D. Samples were taken at each stage and frozen at −80° C. until assayed. Remaining fraction 1 paste was stored at −80° C.

1.1.13 Extraction 3 (Frozen Paste) Procedure

Fraction 1 paste (30 g) was thawed at 37° C. and extracted using heparin paste extraction buffer. The solubilised fraction 1 paste was treated with $Al(OH)_3$ and precipitated using Gly/NaCl buffer. The Gly/NaCl precipitate was then resolubilised using Buffer D. εACA was spiked into samples of the resolubilised Gly/NaCl precipitate at concentrations of 0 mM, 20 mM, 100 mM, 200 mM and 500 mM. The samples were then assessed for stability at 37° C.

Resolubilised Gly/NaCl precipitate was treated with SD and applied to the MacroPrep HQ ion exchange column. Fractions were collected and also assessed for stability at 37° C.

1.1.14 Extraction 4 Procedure

Fraction 1 paste was obtained fresh from production. 40 g was extracted immediately using heparin paste extraction buffer. After 2 hours of extraction, the fraction 1 paste was not completely solubilised. The material was centrifuged* and the supernatant (solubilised fraction 1 paste #1) treated with $Al(OH)_3$ and Gly/NaCl precipitated. The Gly/NaCl precipitate was resolubilised using Buffer D. εACA was spiked into 2 sets of samples of the resolubilised Gly/NaCl precipitate at concentrations of 0 mM, 20 mM, 125 mM, 250 mM and 500 mM. One group of samples was incubated at 37° C. immediately and assessed for stability over time. The other group of samples was stored frozen at −80° C. for 60 hours, thawed and then incubated at 37° C. for stability. The remaining resolubilised Gly/NaCl precipitate was SD treated and applied to the ion exchange column.

*The non-solubilised fraction 1 material (14.13 g) was then re-extracted in heparin paste extraction buffer containing 0.8 M NaCl. The solubilised fraction 1 material (#2) was aliquoted and stored frozen at −80° C.

1.1.15 Addition of ATIII to Extraction Buffer

Fraction 1 paste was obtained from production and half was stored for 4.5 days at 4° C. and the other half at −80° C. In this experiment, extractions were performed using the 4° C. (fresh paste) and the −80° C. (frozen paste) extracted in buffer with and without 1 IU/mL ATIII. An additional change to the standard extraction buffer was the increase in salt concentration to 0.8 M.

Fraction 1 paste (6 g) was extracted under each of the following conditions:

(1) Fresh paste extracted in 20 mM NaCitrate, 5 mM εACA, 0.8M NaCl, pH 7.3.

(2) Fresh paste extracted in 20 mM NaCitrate, 5 mM εACA, 0.8M NaCl, 1 IU/mL ATIII, pH 7.3.

(3) Frozen paste thawed at 37° C. and then extracted in 20 mM NaCitrate, 5 mM εACA, 0.8M NaCl, pH 7.3.

(4) Frozen paste thawed at 37° C. and then extracted in 20 mM NaCitrate, 5 mM εACA, 0.8M NaCl, 1 IU/mL ATIII, pH 7.3.

The solubilised fraction 1 paste was subjected to alhydrogel absorption and precipitated using Gly/NaCl buffer. The precipitates were then split in half. Half the precipitate was stored at −80° C. and the other half was resolubilised using Buffer D. The resolubilised precipitate was then split in half again and 0 εACA or 250 mM εACA was added. The samples were then assessed for stability at 37° C.

The frozen Gly/NaCl ppt was thawed at 37° C. and resolubilised using Buffer D+100 mM εACA (warmed to 30° C.). Resolubilisation was performed at 30° C. The samples were then assessed for stability at 37° C.

1.1.16 Addition of Heparin to Extraction Buffer

Fraction 1 paste was obtained from production after storage for 3 days at 4° C. In this experiment, 4 extractions were performed using buffer with and without 1 IU/mL ATIII in the presence of 20 IU/mL or 60 IU/mL heparin.

Fraction 1 paste (6 g) was extracted under each of the following conditions:

(1) Fresh paste extracted in 20 mM NaCitrate, 5 mM εACA, 0.4 M NaCl, 20 IU/mL heparin pH 7.3.

(2) Fresh paste extracted in 20 mM NaCitrate, 5 mM εACA, 0.4 M NaCl, 60 IU/mL heparin, pH 7.3.

(3) Fresh paste extracted in 20 mM NaCitrate, 5 mM εACA, 0.4 M NaCl, 20 IU/mL heparin, 1 IU/mL ATM, pH 7.3.

(4) Fresh paste extracted in 20 mM NaCitrate, 5 mM εACA, 0.8 M NaCl, 60 IU/mL heparin, 1 IU/mL ATIII, pH 7.3.

The solubilised fraction 1 paste was treated with Al(OH)$_3$ and precipitated using Gly/NaCl buffer. The precipitates were then split in half. Half the precipitate was stored at −80° C. and the other half was resolubilised using Buffer D. The resolubilised precipitate was then split in half again and 0 εACA or 250 mM εACA was added. The samples were then assessed for stability at 37° C.

Resolubilisation of the frozen pellet was performed by the addition of Buffer D+100 mM εACA (warmed to 30° C.) into the frozen Gly/NaCl precipitates. Resolubilisation was performed at 30° C. The samples were then assessed for stability at 37° C.

1.1.17 Paste: Buffer Ratio Study

Study I:

Fraction 1 paste was obtained fresh from production. 1.5 g, 3 g, 4.5 g, 6 g, 7.5 g & 9 g were resolubilised in 50 g of extraction buffer containing 0.8 M NaCl. Samples were taken for total and clottable protein. Remaining material was discarded.

Study II:

Fraction 1 paste (Batch # 3715001253) was obtained fresh from production. 4.5 g, 9 g, 13.5 g, 18 g, 22.5 g & 27 g were resolubilised in 150 mL of extraction buffer containing 0.8 M NaCl, 60 IU/mL heparin at 37° C. for 90 minutes. Samples were taken for total and clottable protein.

1.1.18 Extraction Temperature Study

Fraction 1 paste was obtained fresh from production. 18 g was extracted in 150 mL of 20 mM NaCitrate, 5 mM εACA, 0.8 M NaCl, pH 7.3 for 2 hours at room temperature. Another 18 g was extracted in 150 mL of 20 mM NaCitrate, 5 mM εACA, 0.8 M NaCl, pH 7.3 for 2 hours at 37° C. Samples were taken at 30 min., 60 min., 90 min. and 120 min. throughout the extraction for total and clottable protein. The solubilised paste was then centrifuged and another sample taken.

1.1.19 Production Scale Extraction Study

Production Scale Extraction I:

Fraction 1 paste was obtained fresh from production. 20.0 kg was extracted by PET group in 20 mM NaCitrate, 5 mM εACA, 0.8 M NaCl, 60 IU/mL heparin, pH 7.3 at a ratio of 1 g paste:8.33 g buffer. Extraction was performed at 37° C. for 90 min.

Solubilised fraction 1 paste was then subjected to alhydrogel absorption and Gly/NaCl precipitation were performed. The precipitate was split in two and half the precipitate resolubilised in Buffer D containing 100 mM εACA and the other half frozen at −80° C. The resolubilised Gly/NaCl precipitate was then treated with SD, wet heat treated and applied to the ion exchange column. The eluate was collected, sampled and frozen at −80° C.

Resolubilisation of the frozen pellet was performed by the addition of Buffer D+100 mM εACA (warmed to 30° C.) into the frozen Gly/NaCl precipitates. Resolubilisation was performed at 30° C. The samples were then assessed for stability at 37° C.

Production Scale Extraction II:

Fraction 1 paste was obtained fresh from production. 30.0 kg was extracted by PET group in 20 mM NaCitrate, 5 mM εACA, 0.8 M NaCl, 60 IU/mL heparin, pH 7.3 at a ratio of 1 g paste 8.33 g buffer. Extraction was performed at 37° C. for 90 min. Samples were taken for total and clottable protein.

1.2 Results 1.2.1 Extraction 1 Procedure

Fraction 1 paste (6 g) was solubilised in 50 mL extraction buffer. Following centrifugation, 52.47 g supernatant was collected and the pellet discarded.

Protein Characterisation

The solubilised fraction 1 paste was assayed for total protein, clottable protein, factor XIII, plasminogen and fibronectin as detailed in Table 1. The yield of fibrinogen per kilogram of plasma is calculated in Table 2. Size exclusion analysis was performed using Superose 6, the results of which are detailed in Table 3.

TABLE 1

Protein characterisation of solubilised fraction 1 paste

| Sample | SFP (g) | Protein (mg/mL) | Fibrinogen (mg/mL) | Total fibrinogen (mg) | % CP (%) | FXIII (IU/mL) | Plasminogen (μg/mL) | FN (mg/mL) |
|---|---|---|---|---|---|---|---|---|
| SFP | 52.7 | 26.56 | 17.20 | 902.5 | 65 | 13.57 | 125–129 | 0.44 |

The characterisation of the solubilised fraction 1 paste shows that high levels of protein are extracted of which approximately 65% is clottable protein or fibrinogen. The solubilised fraction 1 paste also contains high levels of factor XIII and plasminogen but has low levels of fibronectin.

TABLE 2

Yield of fibrinogen from solubilised fraction 1 paste

| Sample | Total F1 paste generated (g) | F1 paste extracted (g) | Total fibrinogen (mg) | Mass of starting plasma (kg) | Fibrinogen YIELD (g/kg plasma) |
|---|---|---|---|---|---|
| SFP | 60600 | 6.02 | 902.5 | 7476 | 1.22 |

The yield of fibrinogen from solubilised fraction 1 paste is high in comparison to solubilised heparin paste, with 1.22 g fibrinogen extracted per kilogram of plasma.

TABLE 3

Superose 6 analysis of solubilsed fraction 1 paste

| Sample | % Area aggregate 1 | % Area aggregate 2 | % Area fibrinogen | % Area other LMW proteins |
|---|---|---|---|---|
| SFP | 1.24 | 4.89 | 65.88 | 28.0 |

Superose 6 analysis of solubilised fraction 1 paste shows approximately 65% fibrinogen monomer with low levels of aggregates but the presence of low molecular weight proteins.

SDS-PAGE Analysis

SDS-PAGE analysis results show the presence of high molecular weight proteins under non-reducing conditions and three major bands at approximately 40–60 kDa under reducing conditions. This profile is typical of material rich in fibrinogen.

Stability at 37° C.

The stability of solubilised fraction 1 paste was approximately 24 hours. The solubilised fraction 1 paste sample clotted between 24 hrs and 32 hrs incubation at 37° C.

1.2.2 Extraction 2 Procedure

Fraction 1 paste (12.06 g) was extracted in 100.5 mL extraction buffer, centrifuged, Al(OH)$_3$ absorbed and Gly/NaCl precipitated.

Protein Characterisation

All samples were assayed for total protein, clottable protein, factor XIII, factor II, plasminogen and fibronectin and the yield of fibrinogen per kilogram of plasma calculated (Table 4). Size exclusion analysis was performed using Superose 6, the results of which are detailed in Table 5.

Characterisation of solubilised fraction 1 paste showed extraction of high levels of protein of which approximately 73% was clottable protein. This result is consistent with that obtained from Extraction I. Again, high levels of factor XIII and plasminogen and low levels of fibronectin were also extracted. The yield of fibrinogen per kilogram of plasma was also high at 1.83 g/kg.

Following Al(OH)$_3$ absorption, factor II, which was observed to be 0.53 IU/mL in the solubilised fraction 1 paste, was undetectable. Clottable protein was observed to be 77% and the concentrations of FXIII, plasminogen and fibronectin were relatively unchanged. The yield of fibrinogen per kilogram of plasma decreased by approximately 22% which is an expected result over this step.

Gly/NaCl precipitation increased the purity of the fibrinogen to 92% clottable and removed fibronectin to negligible levels.

TABLE 5

Superose 6 analysis

| Sample | % Area aggregate 1 | % Area aggregate 2 | % Area fibrinogen | % Area other LMW proteins |
|---|---|---|---|---|
| SFP | 10.85 | 4.78 | 52.47 | 31.90 |
| ASFP | 6.32 | 3.20 | 58.86 | 31.62 |
| GASFP | 8.25 | 10.59 | 74.24 | 6.93 |

Superose 6 analysis of in process samples showed the purification of fibrinogen over the Gly/NaCl precipitation step with an increase in the fibrinogen peak from 59% to 74% of the total area.

SDS-PAGE Analysis

SDS-PAGE analysis of solubilised fraction 1 paste showed very similar protein composition to that generated in Extraction 1. SDS-PAGE analysis of in process samples also demonstrated the purification of fibrinogen over the Gly/NaCl step. The resolubilised Gly/NaCl precipitate sample contains fewer high molecular weight protein bands when analysed under reducing conditions and the absence of bands at 200 kDa, 150 kDa, and 55 kDa when analysed under non-reducing conditions.

1.2.3 Extraction 3 (Frozen Paste) Procedure

Fraction 1 paste (21.13 g) was extracted in 176 mL extraction buffer, centrifuged, Al(OH)$_3$ absorbed and Gly/NaCl precipitated. On addition of product to Gly/NaCl buffer, some product clotted. Resolubilised Gly/NaCl precipitate was SD treated, applied to an ion exchange column and the fibrinogen was eluted in a salt-containing buffer.

Protein Characterisation

All samples were assayed for total protein, clottable protein, factor XIII, and factor II and the yield of fibrinogen per kilogram of plasma calculated (Table 6). Size exclusion

TABLE 4

Characterisation summary

| Sample | Protein mg/mL | Fibrinogen mg/mL | Total fibrinogen (mg) | CP % | FXIII IU/mL | FII IU/mL | Plasm μg/mL | FN mg/mL | Fibrinogen YIELD (g/kg plasma) |
|---|---|---|---|---|---|---|---|---|---|
| SFP | 28.11 | 20.42 | 2200 | 73 | 12.61 | 0.53 | 120.35 | 0.64 | 1.83 |
| ASFP | 19.43 | 15.00 | 1706 | 77 | 10.29 | UD# | 100.56 | 0.38 | 1.42 |
| GASFP | 17.63 | 16.26 | 1355 | 92 | 14.98 | UD# | 72.15 | 0.08 | 1.13 | undetected analysis was performed using Superose 6, the results of which are detailed in Table 7.

TABLE 6

Characterisation summary

| Sample | Protein mg/mL | Fibrinogen mg/mL | Total fibrinogen (mg) | % CP | Factor XIII IU/mL | Factor II IU/ml | Fibrinogen g/Kg plasma |
|---|---|---|---|---|---|---|---|
| SFP | clotted | clotted | — | — | clotted | clotted | — |
| ASFP | 17.79 | 10.49 | 2029 | 59 | 6.95 | UD | 0.96 |
| GASFP | 12.21 | 10.07 | 836 | 82 | clotted | UD | 0.40 |
| IEX column eluate | 3.72 | 2.1 | 358 | 56 | — | — | 0.17 | undetected

Characterisation of solubilised fraction 1 paste was not performed as the samples clotted on thawing. One sample of resolubilised Gly/NaCl precipitate also clotted on thawing and as a result no data is available for factor XIII levels at this step.

Samples that were analysed demonstrated similar profiles to the previous extraction experiments. Clottable protein was approximately 60% after Al(OH)$_3$ absorption and increased to greater than 80% after Gly/NaCl precipitation. Factor XIII was present at 7 IU/mL after Al(OH)$_3$ absorption and factor II was undetectable. The yield of fibrinogen per kilogram of plasma was low with only 0.4 g/kg detected after Gly/NaCl precipitation. The GASFP was then applied to the ion exchange column to purify fibrinogen from plasminogen.

TABLE 7

Superose 6 analysis

| Sample | % Area aggregate 1 | % Area aggregate 2 | % Area fibrinogen | % Area other fragments |
|---|---|---|---|---|
| SFP | clotted | clotted | clotted | clotted |
| ASFP | 8.35 | 6.49 | 41.31 | 43.85 |
| GASFP | 6.42 | 19.59 | 63.56 | 10.42 |

Superose 6 analysis showed very high levels of low molecular weight proteins at the Al(OH)$_3$ stage. Purification of fibrinogen was again seen after the Gly/NaCl precipitation with an increase in the fibrinogen content from 40% to 60% of the total area.

SDS-PAGE Analysis

The first sample of solubilised fraction 1 paste was not analysed by SDS-PAGE as the sample clotted on thawing. SDS-PAGE analysis of samples after Al(OH)$_3$ and Gly/NaCl steps, under reducing and non-reducing conditions, shows the purification of fibrinogen. Analysis of the ion exchange column eluate showed that the major protein component is fibrinogen.

Stability at 37° C.

The first sample (24 hrs) of solubilised fraction 1 paste was not analysed by SDS-PAGE as the sample clotted on thawing. The remainder of the solubilised fraction 1 paste stability sample clotted somewhere between 24 hrs and 32 hrs after being left at 37° C. Analysis of the Al(OH)$_3$ sample showed evidence of fibrinogen breakdown at 24 hours.

After Gly/NaCl precipitation, fibrinogen was stable at 44 hours but breakdown was evident at 144 hours (no 72 hour sample was found). When 200 or 500 mM εACA was added to the resolubilised Gly/NaCl precipitate, fibrinogen was stable for greater than 240 hours.

After elution from the ion exchange column, fibrinogen was stable for at least 208 hours (the last time point tested) without the addition of any εACA.

1.2.4 Extraction 4 Procedure

Fresh fraction 1 paste (40.0 g) was extracted in 333 mL extraction buffer, centrifuged, Al(OH)$_3$ absorbed and Gly/NaCl precipitated. εACA was spiked into 2 sets of samples of the resolubilised Gly/NaCl precipitate at concentrations of 0 mM, 20 mM, 125 mM, 250 mM and 500 mM. One group of samples was incubated at 37° C. immediately and assessed for stability over time. The other group of samples was stored frozen at −80° C. for 60 hours, thawed and then incubated at 37° C. for stability. Resolubilised Gly/NaCl precipitate was SD treated, applied to an ion exchange column and the fibrinogen was eluted in a salt-containing buffer.

Protein Characterisation

All samples were assayed for total protein, clottable protein, factor XIII, factor II, and fibronectin and the yield of fibrinogen per kilogram of plasma calculated in Table 8. The pellet remaining after the first extraction was re-extracted with buffer containing 0.8 M NaCl. Protein characterisation of this sample and yield per kg plasma is detailed in Table 9. Superose 6 analysis was not performed.

TABLE 8

Characterisation summary

| Sample | Protein mg/mL | Fibrinogen mg/mL | Total fibrinogen (mg) | % CP | FXIII IU/mL | FII IU/mL | FN mg/mL | Fibrinogen YIELD (g/kg plasma) |
|---|---|---|---|---|---|---|---|---|
| SFP | 23.69 | 16.09 | 5680 | 68 | 11.9 | 0.36 | 0.45 | 1.85 |
| ASFP | 17.39 | 11.68 | 4472 | 67 | 9.0 | UD# | 0.31 | 1.45 |
| GASFP | 19.82 | 17.58 | 4126 | 89 | 15.0 | UD# | 0.06 | 1.35 |
| IEX Elate | 8.49 | 8.00 | 704 | 94 | NT* | NT* | NT* | 1.07 | undetected
not tested

Characterisation of in process samples showed results consistent with previous extractions of fresh fraction 1 paste. Approximately 68% clottable protein was extracted from the fraction 1 paste. Al(OH)$_3$ treatment reduced factor II to undetectable levels and the Gly/NaCl precipitation increased clottable protein to 89% and reduced fibronectin to negligible levels. The yield of fibrinogen per kg plasma at the solubilised fraction 1 paste stage was 1.85 and dropped to 1.35 after Al(OH)$_3$ treatment and Gly/NaCl precipitation, which is expected over these steps. The recovery over the ion exchange chromatography step was approximately 76%.

Frozen GASFP was thawed and applied to the ion exchange column. The eluate was shown to be high in clottable protein and contained low levels of plasminogen. The level of plasminogen in GASFP was not tested therefore the recovery of plasminogen over the ion exchange step cannot be calculated. However, 8 mg/mL fibrinogen and <0.2 μg/mL plasminogen in the eluate equates to less than 1.6 μg/mL in a concentrated product of 60 mg/mL. This result suggests that the ion exchange column is acting efficiently to remove plasminogen from the product.

14.13 g fraction 1 paste (remaining after extraction # 1) was solubilised in 117.7 mL fibrinogen extraction buffer (0.8 M NaCl, pH 7.3).

TABLE 9

Characterisation summary of solubilised fraction 1 paste #2

| Sample | Protein mg/mL | Fibrinogen mg/mL | Total fibrinogen (mg) | % CP | Factor XIII IU/mL | Factor II IU/mL | FN (mg/mL) | Fibrinogen YIELD (g/kg plasma) |
|---|---|---|---|---|---|---|---|---|
| SFP | 26.18 | 17.73 | 2144 | 68 | 12.6 | 0.34 | 0.41 | 0.69 |

Therefore the total yield of fibrinogen per kg of plasma could be calculated as 1.85+0.7 g=2.5 g fibrinogen per kg of plasma at the solubilised fraction 1 paste stage.

SDS-PAGE Analysis

SDS-PAGE analysis shows the presence of fibrinogen in all fractions. After Gly/NaCl treatment, fewer protein bands are observed under reducing conditions demonstrating the purification of the fibrinogen molecule that is also seen by protein characterisation.

Stability at 37° C.

The resolubilised Gly/NaCl precipitate is stable for 64 hours when zero and 20 mM εACA is added to the sample. After 64 hours the sample clotted. With the addition of 125 mM εACA the sample is stable for 72 hours but breakdown of the molecule is evident at the 100 hr time point.

Addition of 250 mM and 500 mM εACA increases the stability of the resolubilised Gly/NaCl precipitate to greater than 124 hrs, the last sample taken.

Resolubilised Gly/NaCl samples spiked with zero or 20 mM εACA and frozen for 60 hours at −80° C. before starting the stability trial, were observed to be less stable than resolubilised non-frozen precipitate. With the addition of zero or 20 mM εACA the samples were stable for 24 hrs after which time they clotted compared to 64 hours in the non-frozen samples. However, the addition of 125 mM, 250 mM and 500 mM εACA increases the stability of the fibrinogen to >96 hrs, the last time point taken, which did not differ significantly from 124 hours seen with the non-frozen sample. Thus, fibrinogen is stable at −80° C. only with the addition of at least 125 mM εACA.

Stability analysis of the ion exchange eluate was shown to be >170 hrs without the addition of εACA.

1.2.5 Addtion of ATIII to Extraction Buffer

Fraction 1 paste (6 g), fresh and frozen, was extracted in 50 mL of the extraction buffer (±1 IU/mL ATIII), centrifuged, Al(OH)$_3$ absorbed and Gly/NaCl precipitated. The precipitate was split in half. Half the precipitate was stored at −80° C. and the other half was resolubilised using Buffer D. The resolubilised precipitate was split in half again and 0 εACA or 250 mM εACA was added. The samples were then assessed for stability at 37° C.

Protein Characterisation

Extraction 1

Fresh fraction 1 paste (6.04 g) was extracted in 50.34 g buffer containing 20 mM NaCitrate, 5 mM εACA, 0.8 M NaCl, pH 7.3. The solubilised fraction 1 paste was then treated with Al(OH)$_3$ and precipitated using Gly/NaCl buffer.

All samples were assayed for total protein and clottable protein and the yield of fibrinogen per kilogram of plasma was calculated (Table 10).

TABLE 10

Characterisation summary

| Sample | Protein mg/mL | Fibrinogen mg/mL | Total fibrinogen (mg) | % clottable protein | Fibrinogen g/Kg plasma |
|---|---|---|---|---|---|
| SFP | 19.56 | 12.14 | 608 | 62 | 0.85 |
| GASFP | 15.15 | 13.20 | 337 | 87 | 0.47 |
| GASFP + 250 mM εACA | 13.89 | 11.84 | 313 | 85 | 0.44 |

Characterisation of in process samples for total and clottable protein was again consistent with previous results. Approximately 60% clottable protein was extracted from fraction 1 paste which was increased to 85% clottable protein after the Gly/NaCl precipitation step. The yield was lower than previous extractions with 0.85 g fibrinogen extracted per kilogram of plasma.

Extraction 2

Fresh fraction 1 paste (5.98 g) was extracted in 49.84 g buffer containing 20 mM NaCitrate, 5 mM εACA, 0.8 M NaCl, 1 IU/ml ATIII pH 7.3. The solubilised fraction 1 paste was then treated with Al(OH)$_3$ and precipitated using Gly/NaCl buffer.

All samples were assayed for total protein and clottable protein and the yield of fibrinogen per kilogram of plasma calculated (Table 11).

TABLE 11

Characterisation summary of solubilised Fraction 1 paste

| Sample | Protein mg/mL | Fibrinogen mg/mL | Total fibrinogen(mg) | % clottable protein | Fibrinogen g/Kg plasma |
|---|---|---|---|---|---|
| SFP | 16.15 | 10.48 | 524 | 65 | 0.74 |
| GASFP | 13.63 | 11.79 | 283 | 86.5 | 0.40 |
| GASFP + 250 mM εACA | 13.76 | 11.86 | 294 | 86 | 0.42 |

Characterisation of in process samples generated using extraction buffer containing 1 IU/mL ATIII was very similar to extraction buffer without ATIII. Approximately 65% clottable protein was extracted from fraction 1 paste which was increased to 85% clottable protein after the Gly/NaCl precipitation step. The yield was also lower than previous extractions with 0.74 g fibrinogen extracted per kilogram of plasma.

Extraction 3

Frozen fraction 1 paste (6.06 g) was thawed and extracted in 50.5 g buffer containing 20 mM NaCitrate, 5 mM εACA, 0.8 M NaCl, pH 7.3. The solubilised fraction 1 paste was then treated with Al(OH)$_3$ and precipitated using Gly/NaCl buffer.

All samples were assayed for total protein and clottable protein and the yield of fibrinogen per kilogram of plasma calculated (Table 12).

TABLE 12

Characterisation summary of solubilised Fraction 1 paste

| Sample | Protein mg/mL | Fibrinogen mg/mL | Total fibrinogen (mg) | % clottable protein | Fibrinogen g/Kg plasma |
|---|---|---|---|---|---|
| SFP | 12.75 | 8.59 | 416 | 67 | 0.59 |
| GASFP | 7.84 | 6.57 | 140 | 84 | 0.20 |
| GASFP + 250 mM εACA | 8.59 | 6.32 | 140 | 74 | 0.20 |

Characterisation of in process samples generated following extraction of frozen fraction 1 paste showed extraction of 67% clottable protein which increased to 84% following Gly/NaCl precipitation. These clottable protein results are consistent between fresh and frozen paste starting material. The yield per kilogram of plasma was lower than that extracted from fresh paste with less than 0.6 g fibrinogen extracted per kilogram of plasma.

Extraction 4

Frozen fraction 1 paste (6.07 g) was thawed and extracted in 50.59 g buffer containing 20 mM NaCitrate, 5 mM εACA, 0.8 M NaCl, 1 IU/mL ATIII, pH 7.3. The solubilised fraction 1 paste was treated with Al(OH)$_3$ and precipitated using Gly/NaCl buffer.

All samples were assayed for total protein and clottable protein and the yield of fibrinogen per kilogram of plasma calculated (Table 13).

TABLE 13

Characterisation summary of solubilised Fraction 1 paste

| Sample | Protein mg/mL | Fibrinogen mg/mL | Total fibrinogen (mg) | % clottable protein | Fibrinogen g/kg plasma |
|---|---|---|---|---|---|
| SFP | 15.90 | 10.34 | 509 | 65 | 0.71 |
| GASFP | 9.73 | 8.21 | 191 | 84 | 0.27 |
| GASFP + 250 mM εACA | 9.60 | 7.14 | 171 | 74 | 0.24 |

Characterisation of in process samples generated after extraction of frozen fraction 1 paste in buffer containing 1 IU/mL ATIII showed very similar results with respect to clottable protein and yield to those obtained from previous extractions±ATIII.

Stability at 37° C.

SDS-PAGE analysis of in process stability samples from each extraction experiment was performed.

The stability (in hrs) of solubilised fraction 1 paste, Al(OH)$_3$ absorbed and Gly/NaCl precipitated samples from fresh (4° C.) and frozen (−80° C.) paste, extracted in buffers with (+) and without (−) ATM are detailed in Table 14 below.

TABLE 14

Stability of fibrinogen (hours)

| | 4° C. | | −80° C. | |
|---|---|---|---|---|
| | −ATIII | +ATIII | −ATIII | +ATIII |
| SFP | 40 | 74 | >112 | >112 |
| ASFP | 63.5 | 92 | >112 | >112 |
| GASFP | >92 | >112 | >112 | >112 |
| GASFP + 250 mM εACA | >112 | >112 | >112 | >112 |

Analysis of Frozen/Thawed/Resolubilised GASFP

The frozen Gly/NaCl precipitate was thawed at 37° C. and resolubilised using Buffer D+100 mM εACA at 30° C. The precipitate resolubilised within 30 min. Samples were then assayed for total and clottable protein in Table 15 below and for stability at 37° C.

TABLE 15

Thawed and resolubilised Gly/NaCl precipitate

| GASFP | Protein (mg/mL) | Fibrinogen (mg/mL) | Total fibrinogen (mg) | clottable protein (%) | Fibrinogen g/kg plasma |
|---|---|---|---|---|---|
| Extraction 1 (4° C.) | 16.21 | 14.18 | 277 | 87 | 0.39 |
| Extraction 2 (4° C., ATIII) | 12.80 | 11.18 | 206 | 87 | 0.29 |
| Extraction 3 (−80° C.) | 12.74 | 10.91 | 195 | 86 | 0.27 |
| Extraction 4 (−80° C., ATIII) | 8.81 | 7.65 | 134 | 87 | 0.19 |

Protein characterisation shows that the freezing of the precipitate does not affect the levels of clottable protein or yield of fibrinogen/kg plasma in the resolubilised Gly/NaCl precipitate.

Stability analysis of the thawed resolubilised Gly/NaCl precipitates showed that the fibrinogen from all extraction conditions was stable for 120 hours. This result is consistent with that of the non-frozen Gly/NaCl precipitates stability.

1.2.6 Addition of Heparin to Extraction Buffer

Fresh fraction 1 paste (6 g) was extracted in 50 g of the appropriate extraction buffer, treated with Al(OH)$_3$ and precipitated using Gly/NaCl buffer. The precipitates were then split in half. Half of the precipitate was stored at −80° C. The other half was resolubilised using Buffer D. The resolubilised precipitates were then split in half again and 250 mM εACA added to one half and no εACA added to the other half. The samples were then assessed for stability at 37° C.

Protein Characterisation

Extraction 1

Fresh fraction 1 paste (6.0 g) was extracted in 50.0 g of extraction buffer containing 20 mM NaCitrate, 5 mM εACA, 0.4 M NaCl, 20 IU/mL heparin, pH 7.3. The solubilised fraction 1 paste was then treated with Al(OH)$_3$ and precipitated using Gly/NaCl buffer.

All samples were assayed for total protein and clottable protein and the yield of fibrinogen per kilogram of plasma was calculated (Table 16).

TABLE 16

Characterisation summary

| Sample | Protein mg/mL | Fibrinogen mg/mL | Total fibrinogen (mg) | % clottable protein | Fibrinogen g/kg plasma |
|---|---|---|---|---|---|
| SFP | 27 | 18.09 | 974 | 67 | 1.67 |
| ASFP | 20.19 | 12.96 | 718 | 64 | 1.23 |
| GASFP | 27.29 | 24.11 | 493 | 88 | 0.85 |
| GASFP + 250 mM εACA | 27.79 | 24.52 | 517 | 88 | 0.89 |

Characterisation of in process samples generated from extraction with buffer containing 20 IU/mL heparin were very similar to those obtained with the original extraction buffer. Clottable protein was again 67% after extraction and increased to 88% after Gly/NaCl precipitation. The yield was high with 1.67 g fibrinogen extracted per kilogram of plasma.

Extraction 2

Fresh fraction 1 paste (6.02 g) was extracted in 50.17 g buffer containing 20 mM NaCitrate, 5 mM εACA, 0.4 M NaCl, 60 IU/ML heparin, pH 7.3. The solubilised fraction 1 paste was treated with Al(OH)$_3$ and then precipitated using Gly/NaCl buffer.

All samples were assayed for total protein and clottable protein and the yield of fibrinogen per kilogram of plasma was calculated (Table 17).

TABLE 17

Characterisation summary

| Sample | Protein mg/mL | Fibrinogen mg/mL | Total fibrinogen (mg) | % clottable protein | Fibrinogen g/kg plasma |
|---|---|---|---|---|---|
| SFP | 24.12 | 16.09 | 858 | 67 | 1.47 |
| ASFP | 19.56 | 13.04 | 707 | 67 | 1.21 |
| GASFP | 25.89 | 23.00 | 440 | 89 | 0.75 |
| GASFP + 250 mM εACA | 25.64 | 22.82 | 451 | 89 | 0.77 |

Characterisation of in process samples from fraction 1 paste extracted with buffer containing 60 IU/mL heparin showed results very similar to the original extraction buffer in terms of total and clottable protein and fibrinogen yield.

Extraction 3

Fresh fraction 1 paste (6.03 g) was extracted in 50.25 g buffer containing 20 mM NaCitrate, 5 mM εACA, 0.4 M NaCl, 20 IU/mL heparin, 1 IU/mL ATIII, pH 7.3. The solubilised fraction 1 paste was then treated with Al(OH)$_3$ and precipitated using Gly/NaCl buffer.

All samples were assayed for total protein and clottable protein and the yield of fibrinogen per kilogram of plasma was calculated (Table 18).

TABLE 18

Characterisation summary

| Sample | Protein mg/mL | Fibrinogen mg/mL | Total fibrinogen (mg) | % clottable protein | Fibrinogen g/Kg plasma |
|---|---|---|---|---|---|
| SFP | 17.92 | 11.43 | 592 | 64 | 1.01 |
| ASFP | 12.97 | 7.97 | 419 | 61 | 0.72 |
| GASFP | 27.16 | 24.41 | 439 | 90 | 0.75 |
| GASFP + 250 mM εACA | 26.27 | 23.25 | 431 | 88 | 0.73 |

Characterisation of in process samples from fraction 1 paste extracted in buffer containing 20 IU/mL heparin and ATIII showed results very similar to the those obtained with the original extraction buffer. The yield was lower with 1 g fibrinogen extracted per kilogram of plasma.

Extraction 4

Fresh fraction 1 paste (6.01 g) was extracted in 50.09 g buffer containing 20 mM NaCitrate, 5 mM εACA, 0.4 M NaCl, 60 IU/mL heparin, 1 IU/mL ATIII, pH 7.3. The solubilised fraction 1 paste was then treated with Al(OH)$_3$ and then precipitated using Gly/NaCl buffer.

All samples were assayed for total protein and clottable protein and the yield of fibrinogen per kilogram of plasma was calculated (Table 19).

TABLE 19

Characterisation summary

| Sample | Protein mg/mL | Fibrinogen mg/mL | Total fibrinogen (mg) | % clottable protein | Fibrinogen g/Kg plasma |
|---|---|---|---|---|---|
| SFP | 23.20 | 14.60 | 774 | 63 | 1.33 |
| ASFP | 18.42 | 12.13 | 659 | 66 | 1.13 |
| GASFP | 18.93 | 16.79 | 281 | 89 | 0.48 |
| GASFP + 250 mM εACA | 19.94 | 17.60 | 305 | 88 | 0.52 |

Once again the results of in process characterisation of total and clottable protein from solubilise fraction 1 paste to Gly/NaCl precipitate were consistent. A significant loss of yield over the Gly/NaCl precipitation stage was noted. Based on previous result, however, the presence of heparin and ATIII is not thought to contribute to the loss over this step.

Stability at 37° C.

The stability of solubilised fraction 1 paste, Al(OH)$_3$ absorbed and Gly/NaCl precipitated samples from fresh paste, extracted in buffers containing 20 IU/mL or 60 IU/mL heparin, with (+) and without (−) ATIII are detailed in Table 20 below.

TABLE 20

Stability of fibrinogen

| extraction buffer # | 20 IU/mL −ATIII (1) | 20 IU/mL +ATIII (3) | 60 IU/mL −ATIII (2) | 60 IU/mL +ATIII (4) |
|---|---|---|---|---|
| SFP | 23 hrs clotted at 39 | 120 hrs | 23 hrs clotted at 63 | >72 hrs |
| ASFP | 39 | 72 | 46 | 72 |
| GASFP | 23 clotted at 39 | 63 clotted at 72 | 120 | 120 |
| GASFP + 250 mM εACA | 120 | 120 | 120 | 120 |

The presence of ATIII in the extraction buffer appears to increase the stability of the samples at 37° C. The presence of 60 IU/mL heparin appears to further enhance this stability to the level obtained after the addition of 250 mM εACA.

Analysis of Frozen/Thawed/Resolubilised GASFP

The frozen Gly/NaCl precipitate was thawed at 37° C. and resolubilised using Buffer D+100 mM εACA at 30° C. The precipitate resolubilised within 30 min. Samples were then assayed for total and clottable protein in Table 21 below and for stability at 37° C.

TABLE 21

Thawed resolubilised Gly/NaCl precipitate

| GASFP | Protein (mg/mL) | Fibrinogen (mg/mL) | Total fibrinogen (mg) | Clottable protein (%) | Fibrinogen g/kg plasma |
|---|---|---|---|---|---|
| Extraction 1 | 29.08 | 25.86 | 548 | 89 | 0.94 |
| Extraction 2 | 28.43 | 25.60 | 555 | 90 | 0.95 |
| Extraction 3 | 28.05 | 25.35 | 542 | 90 | 0.92 |
| Extraction 4 | 18.00 | 16.00 | 330 | 89 | 0.56 |

Protein characterisation shows that the freezing of the precipitate does not affect the levels of clottable protein or yield in the resolubilised Gly/NaCl precipitate. The yield from Gly/NaCl precipitate of Extraction 4 was low but this correlated to the low yield seen in the non-frozen GASFP.

Stability analysis of the thawed resolubilised Gly/NaCl precipitates showed that the fibrinogen from Extraction 1 was stable for at least 36 hrs (last time point), Extraction 2 was stable for at least 72 hrs (last time point), Extraction 3 was stable for at least 72 hrs (last time point), and Extraction 4 was stable for 96 hrs. This result is consistent with that of the non-frozen Gly/NaCl precipitates stability.

1.2.7 Concentration Study
Concentration Study 1

1.5 g, 3 g, 4.5 g, 6 g, 7.5 g & 9 g of fresh fraction 1 paste were resolubilised in 50 g of extraction buffer containing 0.8 M NaCl. All samples were assayed for total protein and clottable protein and the yield of fibrinogen per kilogram of plasma calculated (Table 22).

TABLE 22

Characterisation summary of solubilised Fraction 1 paste

| Sample | Mass of paste (g) ratio | Protein mg/mL | Fibrino-gen mg/mL | Total fibrinogen (mg) | % clottable protein | Fibrinogen g/Kg plasma |
|---|---|---|---|---|---|---|
| SFP #1 | 1.5 (1:33.3) | 8.57 | 4.72 | 233 | 72 | 1.38 |
| SFP #2 | 3 (1:26.7) | 12.57 | 8.51 | 433 | 68 | 1.29 |
| SFP #3 | 4.49 (1:11.1) | 32.50 | 23.40 | 1287 | 72 | 2.56 |
| SFP #4 | 6.03 (1:8.3) | 25.49 | 16.76 | 892 | 66 | 1.32 |
| SFP #5 | 7.51 (1:6.7) | 30.84 | 21.83 | 1202 | 71 | 1.43 |
| SFP #6 | 9.01 (1:5.5) | 19.59 | 13.3 | 693 | 68 | 0.69 |

Regardless of the fraction 1 paste to buffer ratio the levels of clottable protein extracted were similar (see FIG. 1).

Figure 2:
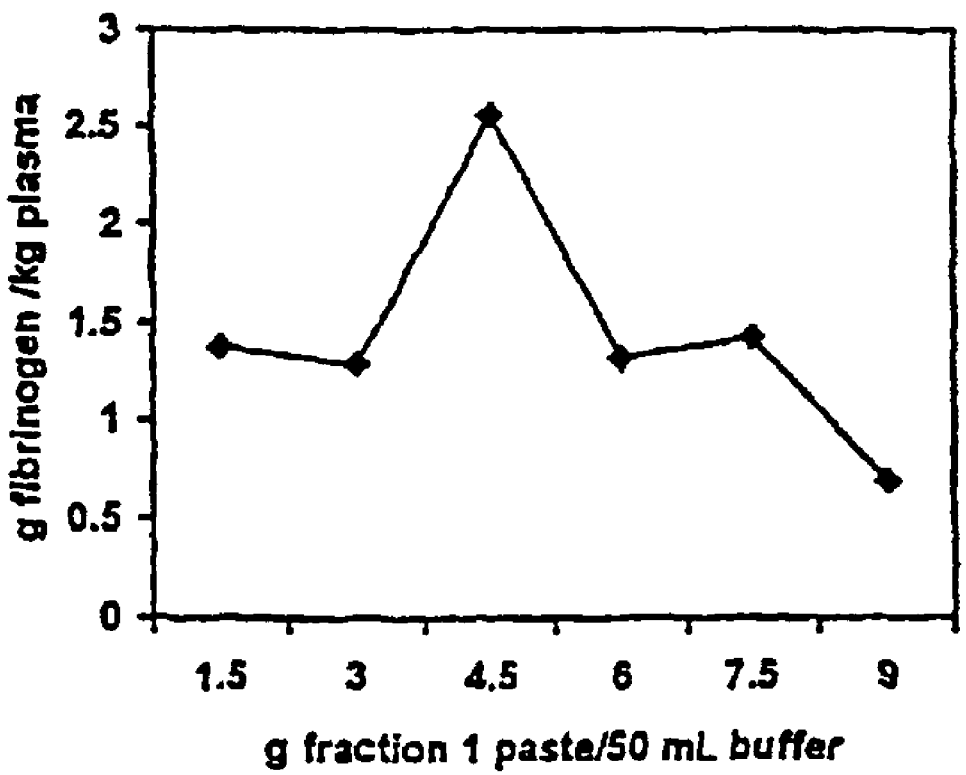
FIG. 2: Yield of total fibrinogen obtained in paste to buffer ratio study (1)

The yield of fibrinogen extracted per kilogram of plasma, however, is not consistent (see FIG. 2).

The maximum yield in this experiment was obtained when a paste to buffer ratio of 1:11.1 was used. After the 2 hour extraction period it was noted that the extraction of 1.5 g, 3 g and 4.5 g fraction 1 paste were completely resolubilised but the extractions of 6 g, 7.5 g and 9 g fraction 1 paste were not. This may suggest that when 4.5 g fraction 1 paste in 50 ML buffer (1:11.1) is extracted completely the maximum levels of fibrinogen are extracted. When the ratio of paste to extraction buffer ratio is increased, not all the fibrinogen present is extracted. Alternatively, the difference in yield of fibrinogen per kilogram of plasma may be due to the non-homogeneous nature of the starting material.

Concentration Study 2

4.5 g, 9 g, 13.5 g, 18 g, 22.5 g & 27 g were resolubilised in 150 mL of extraction buffer containing 0.8 M NaCl, 60 IU/mL heparin at 37° C. for 90 minutes.

All samples were assayed for total protein and clottable protein and the yield of fibrinogen per kilogram of plasma calculated (Table 23).

TABLE 23

Characterisation summary of solubilised fraction 1 paste #2

| Sample | Mass of paste g ratio | Protein mg/mL | Fibrino-gen mg/mL | Total fibrinogen (mg) | % clottable protein | Fibrinogen g/kg plasma |
|---|---|---|---|---|---|---|
| SFP #1 | 4.51 (1.33.3) | 7.08 | 4.71 | 706 | 66 | 1.21 |
| SFP #2 | 9.01 (1:26.7) | 13.45 | 8.81 | 1362 | 65 | 1.17 |
| SFP #3 | 13.50 (1.11.1) | 20.00 | 13.10 | 2073 | 66 | 1.19 |
| SFP #4 | 18.02 (1:8.3) | 25.12 | 16.14 | 2633 | 64 | 1.13 |
| SFP #5 | 22.51 (1:6.7) | 31.99 | 20.31 | 3401 | 63 | 1.17 |
| SFP #6 | 27.01 (1:5.5) | 35.55 | 22.04 | 3787 | 62 | 1.08 |

In this experiment it was noted that after the 90 min. extraction period all fraction 1 paste samples had been completely solubilised.

Regardless of the fraction 1 paste to buffer ratio, the levels of clottable protein extracted were similar (see Table 23).

Figure 3:
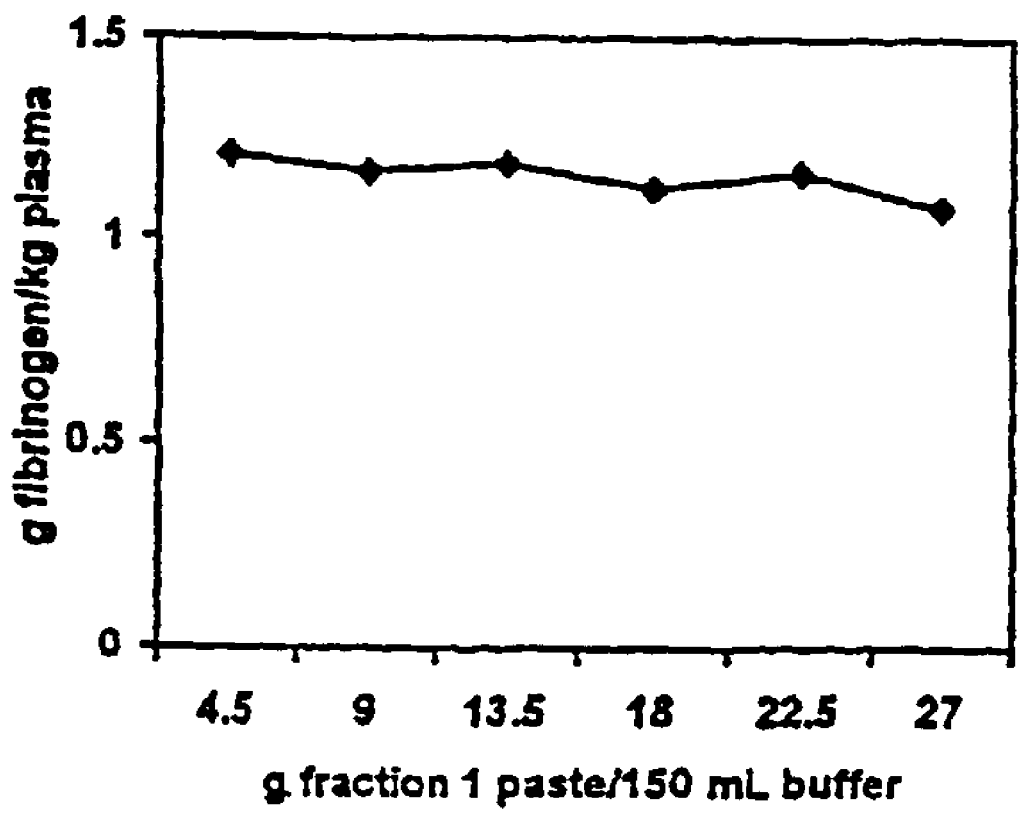
FIG. 3: Yield of total fibrinogen obtained in paste to buffer ratio study (2)

The yield of fibrinogen extracted per kilogram of plasma was also unchanged over the range of paste to buffer ratios (FIG. 3). This suggests that the inconsistent results of the previous experiment (FIG. 2) could be attributed to the non-homogeneous nature of the heparin paste. Furthermore, this data indicates that a higher paste to buffer ratio could be used in the initial extraction resulting in smaller solubilised fraction 1 paste volumes.

1.2.8 Extraction Temperature Study

Fresh fraction 1 paste (18 g) was extracted in 150 mL of buffer (20 mM NaCitrate, 5 mM εACA, 0.8 M NaCl, pH 7.3) at a ratio of 1 g:8.33 g buffer for 2 hours at room temperature and at 37° C. Samples were taken at 30 min., 60 min., 90 min. and 120 min. throughout extraction. The solubilised paste was then centrifuged and another sample taken (125 min).

All samples were assayed for total protein and clottable protein and the yield of fibrinogen per kilogram of plasma calculated (Table 24).

TABLE 24

Characterisation summary of solubilised Fraction 1 paste

| Sample | Mass of paste (g) | Protein mg/mL | Fibrinogen mg/mL | Total fibrinogen (mg) | % clottable protein | Fibrinogen g/Kg plasma |
|---|---|---|---|---|---|---|
| SFP RT - 30' | 17.99 | 8.97 | 6.58 | 1011 | 73 | 0.50 |
| SFP RT - 60' | | 13.06 | 9350 | 1460 | 72 | 0.72 |
| SFP RT - 90' | | 17.87 | 12.88 | 1980 | 72 | 0.98 |
| SFP RT - 120' | | 19.62 | 13.80 | 2121 | 70 | 1.05 |
| SFP RT - 125' | | 20.98 | 15.18 | 2333 | 72 | 1.16 |
| SFP 37° C. - 30' | 18.02 | 22.52 | 15.61 | 2568 | 69 | 1.27 |
| SFP 37° C. - 60' | | 24.66 | 16.79 | 2762 | 68 | 1.37 |
| SFP 37° C. - 90' | | 27.87 | 19.19 | 3157 | 69 | 1.56 |
| SFP 37° C. - 120' | | 27.15 | 18.42 | 3030 | 68 | 1.50 |
| SFP 37° C. - 125' | | 26.32 | 17.75 | 2920 | 67 | 1.44 |

Figure 4:
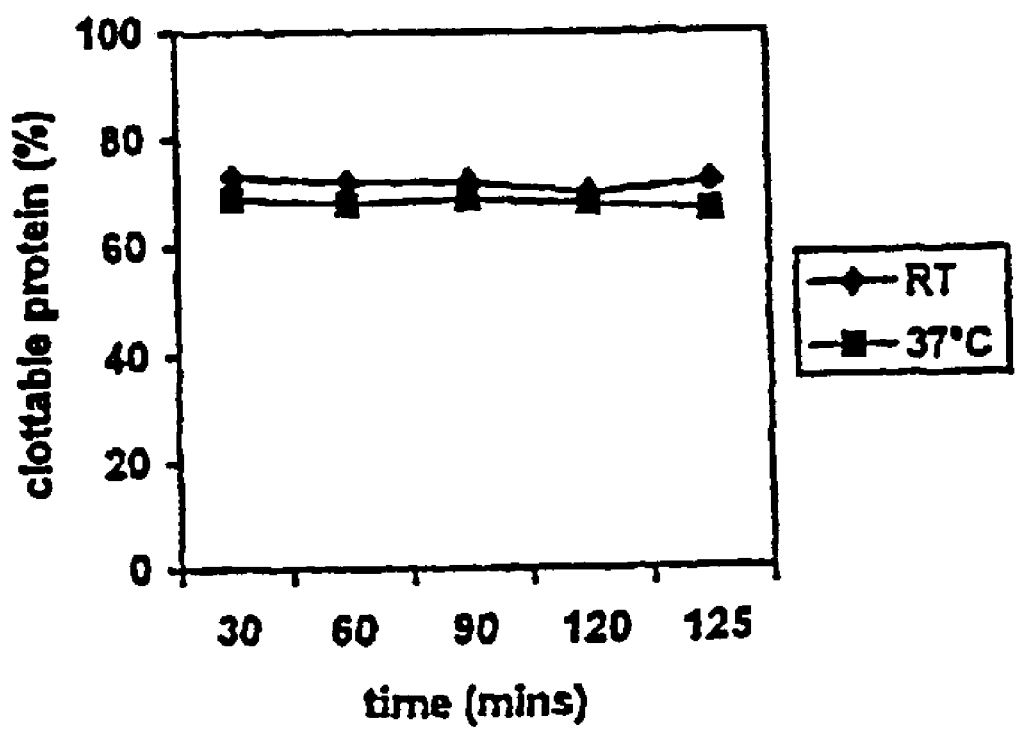
FIG. 4: Yield of clottable fibrinogen obtained over time during extraction of Fraction I paste.

Total and clottable protein extracted at RT and at 37° C. over time was unchanged (see FIG. 4).

Figure 5:
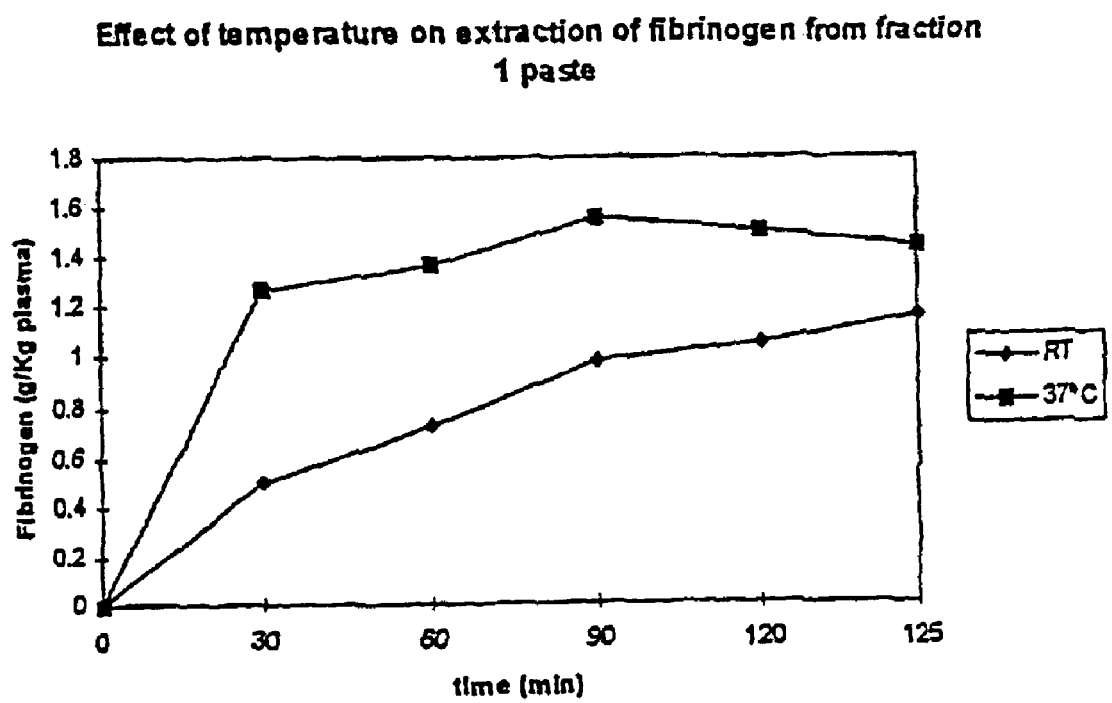
FIG. 5: Effect of temperature on extraction of fibrinogen from Fraction I paste.

However, the yield calculations showed that the level of fibrinogen extracted from fraction 1 paste extracted at 37° C. was higher than that extracted at room temperature at all time points. It was also noted that fraction 1 paste was not completely resolubilised after 2 hr extraction at room temperature but it was completely resolubilised after 2 hr extraction at 37° C. (see FIG. 5 below).

1.2.9 Production Scale Extraction

Extraction 1

Fresh fraction 1 paste (20.0 kg) was extracted at a ratio of 1 g paste: 8.33 g buffer in 20 mM NaCitrate, 5 mM εACA, 0.8 M NaCl, 60 IU/mL heparin, pH 7.3, at 37° C. for 90 min.

Solubilised fraction 1 paste was treated with Al(OH)$_3$ and Gly/NaCl precipitation was performed. The precipitate was split into two and half the precipitate resolubilised in Buffer D containing 100 mM εACA and the other half frozen at −80° C. Half of this resolubilised Gly/NaCl precipitate was then treated with SD, applied to the MacroPrep column. The eluate was collected, sampled and frozen at −80° C. The other half was treated with SD, wet heat treated and applied to the MacroPrep column. The eluate was collected, sampled and frozen at −80° C. The frozen Gly/NaCl pellet was thawed, resolubilised (FTR) and samples for total protein and clottable protein. All samples were assayed for total protein and clottable protein and the yield of fibrinogen per kilogram of plasma calculated (Table 25).

TABLE 25

Characterisation summary

| Sample | Protein mg/mL | Fibrinogen mg/mL | Total fibrinogen (mg) | clottable protein (%) | Plasm. (μg/mL) | Fibrinogen g/kg plasma |
|---|---|---|---|---|---|---|
| SFP | 29.09 | 18.15 | 3386790 | 62 | | 1.78 |
| ASFP | 23.11 | 14.18 | 32363 | 61 | | 1.54 |
| GASFP | 25.91 | 22.66 | 13376 | 87 | 219.6 | 1.27 |
| GASFP ppt (FTR) | 27.74 | 24.2 | 14259 | 87 | | 1.35 |
| Run 1 Eluate | 11.94 | 10.4 | 770 | 87 | 0.66 | 0.97 |
| Run 2 pre wet heat | 1.13 | 0.92 | 691 | 82 | | 0.77 |
| Run 2 post wet heat | 1.36 | 1.11 | 836 | 82 | | 0.93 |
| Run 2 wet heat Eluate | 2.85 | 2.58 | 263 | 91 | 0.42 | 0.30 |

Characterisation of fraction 1 paste extracted at a production scale showed very similar results to that extracted previously at a small lab scale. Approximately 62% clottable protein was extracted at this stage at a yield of 1.78 g fibrinogen per kilogram of plasma. Following Gly/NaCl precipitation the clottable protein again increased to greater than 85%, as expected. (Analysis of the frozen Gly/NaCl precipitate after thawing and resolubilisation showed no loss of total protein, clottable protein or yield of fibrinogen per kg plasma). The material eluted off the column was also high in clottable protein and yield. The plasminogen level of this eluate was very low at 0.66 μg/mL which equates to a 160 fold reduction in the level of plasminogen across this step.

Resolubilised Gly/NaCl precipitate that was wet heat treated and applied to the ion exchange column was high in clottable protein before and after the wet heat treatment. No loss of fibrinogen was seen over the wet heat treatment step. Wet heat treated material, after elution from the ion exchange column, was high in clottable protein but only 30% of the fibrinogen was recovered. Plasminogen levels were also low at 0.42 µg/mL. The results of the ion exchange chromatography of GASFP and wet heat treated GASFP show that the column is acting efficiently to remove plasminogen from the product.

SDS-PAGE Analysis

All samples rich in fibrinogen as seen by the three major bands between 45 and 66 kDa under reducing conditions.

Stability at 37° C.

Stability of in process samples was similar to previous findings (See Appendix for Stability gels). The solubilised fraction 1 paste was stable for approximately 15 hrs. This sample clotted before 39 hrs at 37° C. After $Al(OH)_3$ absorption, the fibrinogen molecule was stable for 48 hrs and after Gly/NaCl precipitation, for >70 hrs. Following elution from the ion exchange column the wet heat treated and non-wet heat treated fibrinogen was stable for at least 113 hrs.

Extraction 2

Fresh fraction 1 paste (30.0 kg) was extracted at a ratio of 1 g paste: 8.33 g buffer in 20 mM NaCitrate, 5 mM εACA, 0.8 M NaCl, 60 IU/mL heparin, pH 7.3, at 37° c. for 90 min.

Total protein and clottable protein were determined and yield per kilogram of plasma calculated in Table 26 below.

Comparison of fraction 1 paste to heparin paste shows a significant increase in yield of fibrinogen generated per kg plasma.

Comparison of fraction 1 paste to heparin paste in terms of stability shows that stability of fibrinogen increases throughout both processes. Final fibrinogen concentrate is equally stable regardless of the starting material.

1.3 Discussion

Fibrinogen was initially extracted from fraction 1 paste at a small scale. Experiments were performed to assess the effect of adding ATIII and heparin to the buffer, and to assess the effect of temperature on the extraction procedure. Results showed that the presence of heparin in the extraction buffer increased the stability of the fibrinogen molecule at this and subsequent steps of the process. Equal stability can also be attained by the addition of at least 125 mM εACA at the resolubilised Gly/NaCl stage.

Performing the extraction at 37° C. was shown to increase the rate of extraction of fibrinogen and the yield of fibrinogen per kilogram of plasma. Thus, the extraction conditions recommended for fraction 1 paste are 20 mM Tri-sodium citrate, 0.8 M NaCl, 5 mM εACA, 60 IU/mL heparin, pH 7.3, extracted for 90 minutes at 37° C.

TABLE 26

Characterisation of solubilised fraction 1 paste

| Total F1 paste generated (g) | F1 paste extracted (g) | Extracted F1 paste (g) | Fibrinogen (mg/mL) | Total fibrinogen (g) | Mass of starting plasma (kg) | Fibrinogen YIELD (g/kg plasma) |
|---|---|---|---|---|---|---|
| 59730 | 30000 | 280000 | 20.64 | 5779.2 | 7728 | 1.49 |

The fraction 1 paste extracted in this experiment was from the same batch as used in the above section entitled "Concentration Study 2". At a small scale, the average yield of fibrinogen per kilogram of plasma was 1.16. At a scale greater than 1,000 times this lab scale the yield is shown to be 1.49 g/kg plasma. This further suggests that the lab scale is not representative of the expected yield at production scale as a result of the non-homogeneous nature of the fraction 1 paste.

The results of the two production scale extractions show that the expected yield of fibrinogen per kilogram of plasma is 1.5–1.8 g/kg.

1.2.10 Comparison of Fraction 1 Paste and Heparin Paste as the Starting Material for Fibrinogen Purification Data gained from experiments detailed in this report is summarised in Table 27 below.

TABLE 27

Comparison of yield from fresh fraction 1 paste and heparin paste extracted at a ratio of 6 g paste to 50 mL buffer

| | Yield | | Stability | |
|---|---|---|---|---|
| Sample | Fraction 1 | Heparin paste | Fraction 1 | Heparin paste |
| Extracted | 1.5 | 0.42 | 24 | <24 |
| Al(OH)3 | 1.32 | N/A | 48 | N/A |
| Gly/NaCl | 0.96 | 0.34 | >70 | 72 |
| Post Wet Heat | 0.85 | 0.26 | >50** | 54 |
| Post Wet Heat column eluate | 0.64* | 0.23 | >113 | 120 |
| Concentrate | 0.58* | 0.21 | >113** | 120 |

*based on expected losses

At a production scale, the extraction of fraction 1 paste was performed on a scale greater than 750 times that of the lab scale. In these large scale experiments, the fraction 1 paste was extracted with the optimised buffer (containing heparin and performed at 37° C.) and the resultant yields were 1.78 g/kg plasma and 1.49 g/kg plasma. The same batch of fraction 1 paste was extracted at both lab and production scale under identical extraction conditions and the yields obtained were 1.15 g/kg and 1.49 g/kg, respectively. With an expected yield of 1.5 g fibrinogen per kilogram of plasma at the solubilised fraction 1 paste stage, the yield from fraction 1 paste is significantly higher that that extracted from heparin paste (0.42 g/kg plasma).

Variation of the fraction 1 paste to extraction buffer ratio suggested in the first small scale experiment that 4.5 g:50 mL buffer (a ratio of 1:11.1) was optimal to obtain the highest yield/kg plasma. However, in a subsequent experiment performed at three times this scale and with the improved extraction buffer, even at the highest paste to buffer ratio (1:5.5) all the fibrinogen was extracted. This result suggests that greater masses of fraction 1 paste may be solubilised in extraction buffer compared to heparin paste (1:8.33) which will result in smaller total extraction volumes.

The protein characterisation of solubilised fraction 1 paste showed similarities and differences to solubilised heparin paste. The amount of clottable protein obtained from either starting material is similar at approximately 65%. Levels of plasminogen and factor XIII were higher in solubilised fraction 1 paste than those extracted from heparin paste, however, the level of fibronectin was significantly lower. When the solubilised fraction 1 paste was further processed using the heparin paste method the material behaved in a similar manner to heparin paste material over the subsequent purification steps. Alhydrogel absorption demonstrated the reduction of factor II to undetectable levels that correlated with an increase in fibrinogen stability at 37° C. Gly/NaCl precipitation resulted in the purification of fibrinogen to greater than 80% clottable protein and the reduction of fibronectin to negligible levels. Ion exchange chromatography was shown to reduce plasminogen to negligible levels in the eluate and increase the stability of the fibrinogen to approximately 120 hrs which is equivalent to heparin paste eluate stability.

As fraction 1 paste is a by-product of another production process it is advantageous to hold the product at this stage prior to commencing the fibrinogen manufacturing process. Heparin paste, a by-product of factor VIII concentrate can be stored frozen for up to 13 months at −80° C. without affecting the resultant levels of clottable protein once extracted.

The stability of frozen fraction 1 paste as a starting material is promising. After processing as far as the ion exchange column, the product demonstrated excellent stability (>208 hrs). In a subsequent experiment (Section 4.5), frozen fraction 1 paste was extracted in the presence and absence of ATIII. No handling problems were encountered after extraction of frozen fraction 1 paste, in either buffer, and the stability of SFP and ASFP was far greater than that observed for previous or subsequent experiments.

Experiments were also performed to assess the possibility of holding the process at the Gly/NaCl precipitate stage prior to resolubilisation. Results of Gly/NaCl pellet, frozen at −80° C. and subsequently thawed and resolubilised, showed that this hold point did not compromise product quality with respect to clottable protein, stability or yield.

Winkleman et al., 1989. Initially, the frozen resolubilised Gly/NaCl precipitate (−80° C.) was thawed in a waterbath at 30° C. To 40 g of resolubilised Gly/NaCl precipitate was added 2.19 g of stock detergent solution and 132 mg of TNBP. The sample was then diluted using sample dilution buffer (25 mM Tris, pH 8.0) until the conductivity was below 10.5 mS/cm. Finally, the sample was filtered through a 0.8 μm membrane filter. Each sample was prepared immediately prior to the start of each run. Failure to dilute the sample often results in a large unbound peak i.e. some fibrinogen is eluted in the unbound.

2.1.2 MacroPrep HQ Purification

The following chromatographic conditions were used to purify the resolubilised gly/NaCl paste:
Bed Height—approx. 20 cm
Column Volume—approx. 100 ml
Flow rate—10 ml/min (~113 cm/hr)
Detection—UV @ 280 nm
Chromatographic Method
Equilibration: ≧1.5 CV of MQ buffer and when conductivity (post-column) is 90–110% of the prepared buffer.
Load Sample
Wash: 6 CV of MQ buffer.
Elution: ME buffer—Buffer D & 200 mM NaCl, pH 7.0
Regeneration: 2 CV of 1 M NaCl
2.2 Results
2.2.1 Purification Using Wash Buffer (MQ—25 mM Tris, 100 mM NaCl, pH 8.0).

Duplicate runs were performed using 25 mM Tris, 100 mM NaCl, pH 8.0 as the wash (MQ) buffer. Samples were loaded on a MacroPrep column and the collected fractions analysed. Results are shown in Table 28.

TABLE 28

MQ-25 mM Tris 100 mM NaCl, pH 8.0

| Pool | Total Protein (mg/ml) | Clottable Protein (mg/ml) | Plasminogen (ug/ml) | Non Clottable Protein | Ratio of Fibrinogen to Plasminogen | Total Volume (ml) | Cumulative % recovery Fibrinogen | Cumulative % recovery Plasminogen | % Clottable Protein per fraction | % Clottable Protein culm |
|---|---|---|---|---|---|---|---|---|---|---|
| F08 10a | | | | | | | | | | |
| Pool 80–88 | 4.62 | 3.86 | 0.952 | 0.54 | 4055 | 90 | 57% | 6.8% | 84% | 84% |
| Tube 89 | 1.6 | 0.86 | 0.767 | 0.51 | 1121 | 10 | 58% | 7.4% | 54% | 76% |
| Pool 90–94 | 1.54 | 0.75 | 0.408 | 0.52 | 1838 | 50 | 64% | 9.0% | 49% | 70% |
| Pool 95–100 | 1.44 | 0.7 | <0.2 | 0.49 | 7000 | 60 | 71% | 9.5% | 49% | 67% |
| Pool 101–106 | 1.25 | 0.62 | <0.2 | 0.45 | 6200 | 60 | 77% | 9.9% | 50% | 65% |
| F09 10a | | | | | | | | | | |
| Pool 81–86 | 9.75 | 8.73 | 1.68 | 0.45 | 5196 | 60 | 63% | 5.9% | 90% | 90% |
| Pool 87–89 | 2.64 | 1.88 | 1.15 | 0.47 | 1635 | 30 | 70% | 7.3% | 71% | 86% |
| Pool 90–95 | 1.67 | 0.92 | 0.47 | 0.46 | 1957 | 60 | 76% | 9.5% | 55% | 82% |
| Pool 96–108 | 1.38 | 0.65 | <0.2 | 0.47 | | 130 | 87% | 10.2% | 47% | 79% |

The results presented herein show that Fraction I paste is a suitable starting material for the purification of fibrinogen, and has the potential to increase the yield of final product three fold compared to heparin paste.

EXAMPLE 2

Separation of Fibrinogen from Plasminogen Using Ion-Exchange Chromatography 2.1 Materials and Methods
2.1.1 Sample Preparation A Gly/NaCl precepitate was obtained from cryoprecipitate using a modification of the methods described in The average recovery of fibrinogen was 82% and plasminogen was 10%. These figures were used as a bench mark to judge the success of any further modifications to the process.

2.2.2 Addition of EACA to Load Sample.

With large scale production, not all of the samples can be processed in a single ion exchange run and hence some diluted samples were left at room temperature while other samples are purified. It was discovered that the samples were breaking down during this period.

The addition of 100 mM ε-amino caproic acid, EACA (in respect to the volume of undiluted resolubilised Gly/NaCl paste) to the sample increased the stability of the sample from between 0–15 hr to 15–23 hr. There were no significant changes in the chromatographic profile and the recovery of fibrinogen was 93%.

2.2.3 Addition of EACA and Lysine to Wash (MQ) Buffer.

The following wash buffers were used in the purification protocol: (i) 50 mM Tris, 20 mM Lysine, 100 mM NaCl, pH 8.0 and (ii) 50 mM Tris, 20 mM EACA, 100 mM NaCl, pH 8.0. Samples were purified using the Macroprep column and the collected fractions compared. Results are shown in Table 29 below.

TABLE 29

Addition of EACA & Lys to MQ Buffer

| | Buffer | Protein mg/ml | Non Clottable mg/ml | Clottable Protein mg/ml | % Protein as Clottable | Clottable Recovery* | Stability (hrs) |
|---|---|---|---|---|---|---|---|
| F14 10b | | | | | | | |
| Fraction 1 | 20 mM Lys, 50 mM Tris | 10.06 | 0.76 | 9.30 | 92% | | 48–71 |
| Fraction 2 | 100 mM NaCl, pH 8.0 | 2.30 | 0.37 | 1.94 | 84% | 51.67% | 48–71 |
| Fraction 3 | | 1.64 | 0.32 | 1.32 | 80% | | N/A |
| Fraction 4 | | 2.08 | 0.14 | 1.92 | 93% | | N/A |
| F14 10a | | | | | | | |
| Fraction 1 | 20 mM Lys, 50 mM Tris | 9.58 | 0.73 | 8.85 | 92% | | 48–71 |
| Fraction 2 | 100 mM NaCl, pH 8.0 | 1.66 | 0.29 | 1.37 | 83% | 53.19% | 48–71 |
| Fraction 3 | | 1.71 | 0.18 | 1.52 | 89% | | N/A |
| F15 10a | | | | | | | |
| Fraction 1 | 20 mM Lys, 50 mM Tris | 9.50 | 0.77 | 8.73 | 92% | | 48–71 |
| Fraction 2 | 100 mM NaCl, pH 8.0 | 2.88 | 0.40 | 2.48 | 86% | 49.11% | 41–78 |
| Fraction 3 | | 1.63 | 0.32 | 1.31 | 80% | | N/A |
| Fraction 4 | | 1.89 | 0.18 | 1.71 | 90% | | N/A |
| F20 10a | | | | | | | |
| Fraction 1 | 20 mM EACA, 50 mM Tris | 13.27 | 0.80 | 12.47 | 94% | | 71–91 |
| Fraction 2 | 100 mM NaCl, pH 8.0 | 2.85 | 0.35 | 2.30 | 87% | 72.12% | 71–91 |
| Fraction 3 | | 1.57 | 0.29 | 1.28 | 81% | | N/A |
| Fraction 4 | | 1.51 | 0.08 | 1.45 | 96% | | N/A |
| F20 10b | | | | | | | |
| Fraction 1 | 20 mM EACA, 50 mM Tris | 13.02 | 0.77 | 12.24 | 94% | | 71–91 |
| Fraction 2 | 100 mM NaCl, pH 8.0 | 2.51 | 0.38 | 2.15 | 86% | 70.41% | 71–91 |
| Fraction 3 | | 1.81 | 0.29 | 1.32 | 82% | | N/A |
| Fraction 4 | | 1.52 | 0.05 | 1.47 | 97% | | N/A |

NB: In these trials EACA was not added to the sample.

With the addition of 20 mM EACA and 25 mM Tris to the MQ buffer, the stability of the collected fractions increased to between 71–91 hours and the recovery of clottable protein was 71.3%. The longer stability could possibly be attributed to the removal of plasminogen. The unbound region of the chromatogram showed a small UV absorbance.

The average clottable protein recovery decreased to 51.3% when 20 mM lysine and 25 mM Tris were added to the MQ buffer. In the chromatographic profile, the absorbance during the wash step was larger than that obtained using MQ. Hence it can be assumed that the addition of lysine and tris to MQ caused fibrinogen to elute in the unbound peak. The stability of the collected fractions were between 48–71 hours.

These results show that the addition of EACA and an increase of tris concentration in MQ increased the recovery of clottable protein and stability of column eluate.

2.2.4: Varying MQ Buffer Composition

The aim of this experiment was to investigate the effectiveness of the addition of lysine and EACA to the MQ buffer and to examine the effect of the addition of EACA to the sample. Table 30 summarises the Fraction 1 results.

TABLE 30

Results of Varying Wash Buffer Composition

| Sample | EACA in Sample | Buffer MQ plus | Protein recovery % | Plasminogen ug/ml | Stability Hrs |
|---|---|---|---|---|---|
| HPPC04 | No | — | 77 | 5 | 24 |
| HPPC06 | No | — | 78 | 2.3 | 24–47 |
| HPPC06 | No | Lys & Tris | 48 | 0.25 | 47 |

TABLE 30-continued

Results of Varying Wash Buffer Composition

| Sample | EACA in Sample | Buffer MQ plus | Protein recovery % | Plasminogen ug/ml | Stability Hrs |
|---|---|---|---|---|---|
| HPPC04 | Yes | Lys & Tris | 47 | <0.5 | 41 |
| HPPC06 | Yes | Lys & Tris | 49 | 0.27 | 68–93 |
| HPPC04 | Yes | EACA & Tris | 68 | <1.0 | 113–143 |
| HPPC06 | Yes | EACA & Tris | 79 | 0.23 | >141 |
| HPPC06 | Yes | 25 mM Tris | 77 | 0.8 | 66 |

These results show that when no EACA was added to the sample, and MQ (25 mM Tris, 100 mM NaCl, pH 8.0) was used as the wash buffer, the average protein recovery of fraction 1 for HPPC04 & HPPC06 was 77% & 78% respectively. The stability was approximately 24 hours for HPPC04 and <47 hours for HPPC06.

Where 25 mM Tris was added to the MQ buffer, the protein recovery was similar to that obtained using MQ but the stability of the collected fraction was increased to 66 hours.

With the addition of lysine to the MQ buffer (50 mM Tris, 20 mM Lysine 100 mM NaCl, pH 8.0), the average protein recovery of fraction 1 for HPPC06 was 48% and the stability was <47 hours. The plasminogen recovery was reduced dramatically from 10.2% to less than 0.5%.

When EACA was added to the sample prior to loading onto the Macroprep column, and the wash buffer was MQ with lysine, the protein and plasminogen recoveries were approximately the same as those obtained where EACA was not added to the sample. The stability of the eluate, however, was increased from <47 hours to between 68–93 hours for HPPC06 and 41 hours for HPPC04.

Where EACA was added to the samples and the wash buffer was 50 mM Tris, 20 mM EACA 100 mM NaCl, pH 8.0, the protein recoveries were similar to those obtained when using MQ i.e 68% for HPPC04 and 79% for HPPC06. The significant difference was the stability of the collected fractions. The stability was in excess of 113 hours as compared to approximately 24 hours when using MQ buffer.

These results show that the wash buffer containing 50 mM Tris, 20 mM EACA 100 mM NaCl, pH 8.0 gave good results. In particular, the collected fraction had high protein recovery, low plasminogen recovery and long stability.

2.2.5 Stability of MacroPrep Fractions, Individually and Pooled.

Previously, four fractions were collected from the MacroPrep eluate. The following experiment was designed to determine whether the fractions can be pooled in order to increase recovery. The collected fractions were placed on stability both individually and pooled in the ratio as if one fraction was collected.

The purification method involved the use of 50 mM Tris, 20 mM EACA 100 mM NaCl as the wash buffer and EACA was added to the samples prior to loading on the MacroPrep column. The results are shown in Table 31.

In general, Table 31 shows that the first fraction is generally more stable than the later fractions. This is most probably due to the later fractions being considerably less concentrated than fraction 1 and not

TABLE 31

Results of Fraction Pooling

| Sample | Fraction | Total Protein mg/ml | Clottable Protein mg/ml | Plasminogen ug/ml | Protein Total mg | Protein Recovery | Clottable protein Total mg | Clottable protein Recovery | Clottable protein % Clottable | Plasminogen- Total ug | Plasminogen- Recovery | Ratio Fibrin.: Plasm. | Stability Hrs |
|---|---|---|---|---|---|---|---|---|---|---|---|---|---|
| F17 11a | | | | | 767.3 | | 690.6 | | | 2446.5 | | | |
| | 1 | 12.94 | 12.22 | 0.9 | 530.54 | 69% | 501.02 | 73% | 94% | 36.9 | 1.5% | 13578 | >95 |
| | 2 | 2.08 | 1.71 | 0.1 | 72.8 | 9% | 59.85 | 9% | 82% | 3.5 | 0.1% | 17100 | 46–71 |
| | 3 | 1.12 | 0.86 | 0.1 | 140 | 18% | 107.5 | 16% | 77% | 12.5 | 0.5% | 8600 | <22 |
| | 4 | 0.63 | 0.62 | 0.1 | 20.79 | 3% | 20.46 | 3% | 98% | 3.3 | 0.1% | 6200 | <22 |
| | Unbound | 1.61 | 0.75 | 0.48 | 54.74 | 7% | 25.5 | 4% | 47% | 16.32 | 0.7% | 1563 | N/A |
| | Unbound 2 | 1.48 | 0.62 | 0.1 | 50.32 | 9% | 21.08 | 4% | 42% | 3.4 | 0.1% | 6200 | N/A |
| | F1 & 2 | 7.95 | 7.39 | 0.53 | 14.71 | | 13.67 | | 93% | 0.99 | | 13882 | 46–71 |
| | F1, 2 & 3 | 3.73 | 3.35 | 0.26 | 18.07 | | 16.25 | | 90% | 1.29 | | 12649 | 71 |
| | F1, 2, 3, & 4 | 3.29 | 2.96 | 0.24 | 18.57 | | 16.75 | | 90% | 1.37 | | 12271 | 96 |
| F17 11b | | | | | 782.4 | | 704.2 | | | 2494.5 | | | |
| | 1 | 11.34 | 10.47 | 0.55 | 589.68 | 75% | 544.44 | 77% | 92% | 26.6 | 1.1% | 19036 | 46–71 |
| | 2 | 1.87 | 1.51 | 0.1 | 65.45 | 8% | 52.85 | 8% | 81% | 3.5 | 0.1% | 15100 | 22–46 |
| | 3 | 1.07 | 0.77 | 0.1 | 115.56 | 15% | 83.16 | 12% | 72% | 10.8 | 0.4% | 7700 | <71 |
| | 4 | 0.69 | 0.67 | 0.1 | 22.77 | 3% | 22.11 | 3% | 97% | 3.3 | 0.1% | 6700 | <71 |
| | F1 & 2 | 7.54 | 6.88 | 0.37 | 12.59 | | 11.48 | | 91% | 0.62 | | 18609 | 71–95 |
| | F1, 2 & 3 | 3.95 | 3.48 | 0.22 | 21.35 | | 18.85 | | 88% | 1.19 | | 15855 | 71 |
| | F1, 2, 3, & 4 | 3.47 | 3.08 | 0.20 | 21.99 | | 19.47 | | 89% | 1.28 | | 15197 | 71 |
| F19 11a | | | | | 753.7 | | 599.4 | | | 1953.3 | | | |
| | 1 | 9.02 | 8.45 | 0.1 | 595.32 | 79% | 557.7 | 93% | 94% | 6.6 | 0.3% | 84500 | >95 |
| | 2 | 1.7 | 1.44 | 0.1 | 54.4 | 7% | 46.08 | 8% | 85% | 3.2 | 0.2% | 14400 | 47 |
| | 3 | 1 | 0.8 | 0.1 | 98 | 13% | 78.4 | 13% | 80% | 9.8 | 0.5% | 8000 | <23 |
| | 4 | 0.6 | 0.6 | 0.1 | 19.2 | 3% | 19.2 | 3% | 100% | 3.2 | 0.2% | 6000 | <23 |
| | Unbound | 1.3 | 0.58 | 0.33 | 39 | 5% | 17.4 | 3% | 45% | 7.5 | 0.4% | 2320 | N/A |
| | Unbound 2 | 1.44 | 0.6 | 0.1 | 46.08 | 8% | 19.2 | 3% | 42% | 3.2 | 0.2% | 6000 | N/A |
| | F1 & 2 | 6.63 | 6.16 | 0.10 | 20.28 | | 18.85 | | 93% | 0.31 | | 61592 | <23 |
| | F1, 2 & 3 | 3.81 | 3.48 | 0.10 | 23.34 | | 21.30 | | 91% | 0.61 | | 34796 | 71–95 |
| | F1, 2, 3 & 4 | 3.36 | 3.08 | 0.10 | 23.94 | | 21.90 | | 91% | 0.71 | | 30751 | 95–119 |
| F19 11b | | | | | 727.7 | | 578.7 | | | 1885.9 | | | |
| | 1 | 8.68 | 8.16 | 0.1 | 581.56 | 80% | 546.72 | 94% | 94% | 6.7 | 0.4% | 81600 | >119 |
| | 2 | 1.76 | 1.76 | 0.1 | 56.32 | 8% | 56.32 | 10% | 100% | 3.2 | 0.2% | 17600 | 23–47 |
| | 3 | 1 | 1 | 0.1 | 97 | 13% | 97 | 17% | 100% | 9.7 | 0.5% | 10000 | <23 |
| | 4 | 0.6 | 0.6 | 0.1 | 19.2 | 3% | 19.2 | 3% | 100% | 3.2 | | 6000 | <23 |
| | F1 & 2 | 6.37 | 6.03 | 0.10 | 19.12 | | 18.08 | | 95% | 0.30 | | 60267 | >119 |
| | F1, 2, & 3 | 3.69 | 3.51 | 0.10 | 22.12 | | 21.08 | | 95% | 0.60 | | 35133 | 71–95 |
| | F1, 2, 3, & 4 | 3.25 | 3.10 | 0.10 | 22.72 | | 21.68 | | 95% | 0.70 | | 30971 | 95–119 |

Samples F17 11a & F17 11b used resolubilised Gly/NaCl precipitate Batch No. HPPC04 and F19 11a & F19 11b used resolubilised Gly/NaCl precipitate Batch No. HPPC06.

because of the composition of the fractions. This was further examined by pooling the fractions at the same ratio as they were eluted from the column.

When the four fractions were pooled the stability was equivalent to that of fraction 1. By pooling all four fractions, the recovery of protein was increased by approximately 25%.

2.2.6 Modification of the Elution Buffer

Results described in 2.2.5 above show that the fractions eluting from the MacroPrep column can be pooled. The profile of the bound fraction shows a large peak with tailing and then a second peak when the column is washed with 1M NaCl. The second peak is the compression of the tailing due to the higher ionic strength of the 1M NaCl. It was decided to increase the ionic strength of the elution buffer to elute fibrinogen as a single peak. The concentration of NaCl in the ME buffer was therefore increased from 300 mM to 500 mM, 750 mM and 1M. Results are shown in Table 32.

TABLE 32

Increasing NaCl Concentration in ME Buffer

| Sample | ME Buffer NaCl | Fraction | Total Protein | | | Clottable protein | | | | | Stability Hrs |
|---|---|---|---|---|---|---|---|---|---|---|---|
| | | | Total mg | Recovery | Cumulative | Total mg | Recovery | Cumulative | % Clottable | Pool % Clottable | |
| F08 12a | 300 mM | | 559.5 | | | 493.8 | | | | | |
| | | 1 | 439.66 | 79% | 79% | 409.26 | 83% | 83% | 93% | 93% | 90 |
| | | 2 | 101.64 | 18% | 97% | 88.44 | 18% | 101% | 87% | 92% | 72 |
| F09 12a | 500 mM | | 615.5 | | | 543.2 | | | | | |
| | | 1 | 655.6 | 107% | 107% | 599.5 | 110% | 110% | 91% | 91% | >100 |
| F09 12b | 500 mM | | 615.5 | | | 543.2 | | | | | |
| | | 1 | 533.9 | 87% | 87% | 478.42 | 88% | 88% | 90% | 90% | >100 |
| F10 12a | 750 mM | | 654.7 | | | 577.8 | | | | | |
| | | 1 | 498 | 76% | 76% | 447.6 | 77% | 77% | 90% | 90% | >100 |
| | | 2 | 46.9 | 7% | 53% | 34.51 | 6% | 83% | 74% | 88% | >100 |
| F11 12a | 1 M | | 615.5 | | | 543.2 | | | | | |
| | | 1 | 570.6 | 93% | 93% | 516.24 | 95% | 95% | 90% | 90% | >100 |

The addition of an extra 200 mM NaCl to the elution buffer, ME, was sufficient to elute the fibrinogen in a single peak, with very little tailing. There was no significant difference in the characterization results of the collected fraction. Although, the ME buffer with 750 mM and 1 M NaCl also work, it is preferred that ME with 500 mM be used due to the requirements of the following steps in the purification process.

2.2.7 Effect of EACA in Sample on Column Eluate Stability and Recoveries

The aim of this experiment was to compare the bound fractions eluted off the MacroPrep column from samples (resolubilised Gly/NaCl precipitate) containing either 100 or 200 mM EACA.

Results showed that the protein recovery (93.7%, 95.4%), clottable protein (96.0%,99.2%), plasminogen (both were <0.2 ug/ml) and stability results (both were >7 days) were equivalent for the fractions collected from both samples. In other words, similar results were obtained for resolubilised Gly/NaCl samples containing 100 or 200 mM εACA.

Figure 6:
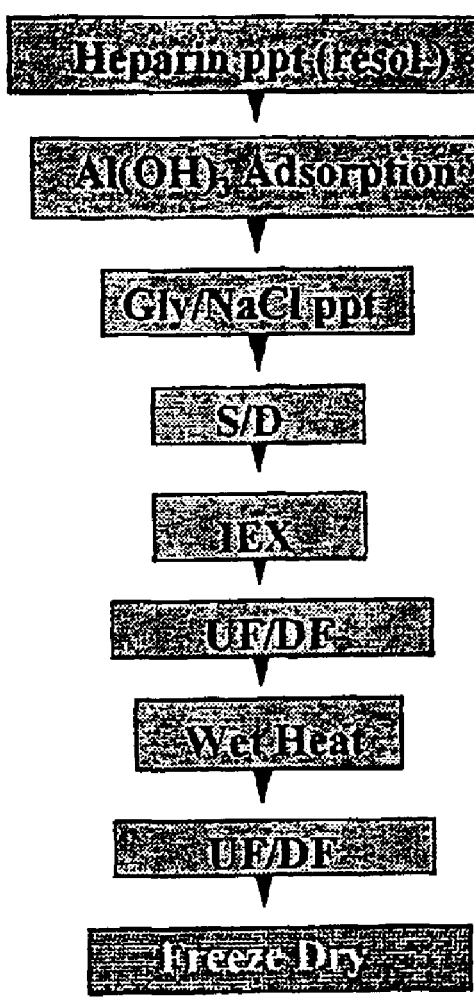
FIG. 6: Flow chart depicting a preferred fibrinogen purification process incorporating the ion-exchange chromatography method of the present invention.

A preferred fibrinogen purification process incorporating the ion-exchange chromatography method described above is shown in FIG. 6.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

References

Blomback and Blomback (1956). *Ark Kemi.* 10:415–43.
Deutsch and Mertz. (1970). Science, 170:1095–6.
Holm at al (1985). *Thrombosis Research,* 37:165–176.
Jakobsen and Kieruif, (1973). *Thrombosis Research,* 3:145–159.
Kuyas, Haeberli, Walder and Straub, (1990). *Thrombosis & Haemostasis,* 64(3).439–444.
Mosesson. (1962). Biochim. Biophys. Acta, 57:204–213.
Robbins, Sunmnaria, Elwyn and Barlow. (1965). J. Biol. Chem, 240:541.
Stathalis et al (1978). *Thrombosis Research,* 13:467–475.
Takeda, (1966). *J. Clin. Investigation,* 45:103–111.
Vuento et al (1979), *Biochemistry J,* 183:331–337

What is claimed is:

1. A method for purifying fibrinogen, the method comprising extracting fibrinogen from a Fraction I precipitate by admixing the Fraction I precipitate with an extraction buffer such that fibrinogen is solubilized in the extraction buffer, wherein the extraction buffer comprises salt at a concentration of at least 0.1 M and heparin at a concentration of at least 10 IU/ml.

2. A method according to claim 1 wherein the concentration of salt is at least 0.4 M.

3. A method according to claim 1 wherein the salt is selected from the group consisting of chloride salts, phosphate salts, acetate salts and a combination thereof.

4. A method according to claim 1 wherein the salt is NaCl.

5. A method according to claim 1 wherein the concentration of heparin is at least about 20 IU/ml.

6. A method according to claim 1 wherein the concentration of heparin is at least about 60 IU/ml.

7. A method according to claim 1 wherein the extraction buffer further comprises Tri-sodium citrate at a concentration of about 20 mM.

8. A method according to claim 1 wherein the extraction buffer further comprises at least one ω-amino acid.

9. A method according to claim 8 wherein the at least one ω-amino acid is present in the extraction buffer at a concentration of at least 5 mM.

10. A method according to claim 1 wherein the extraction buffer further comprises antithrombin III (ATIII) at a concentration of at least about 1 IU/ml.

11. A method according to claim 1 wherein the extraction buffer comprises Tri-sodium citrate at a concentration of about 20 mM, NaCl at a concentration of about 0.8 M, heparin at a concentration of about 60 IU/ml and at least one ω-amino acid at a concentration of about 5 mM.

12. A method according to claim 1 wherein the extraction buffer has a pH of about 7.3.

13. A method according to claim 1 wherein the extraction of fibrinogen is performed at about 37° C.

14. A method according to claim 1, the method further comprising the step of incubating the extracted fibrinogen in solution with aluminium hydroxide followed by centrifugation and removal of the precipitate.

15. A method according to claim 1, the method further comprising the step of precipitating the fibrinogen in the extracted fibrinogen solution by the addition of glycine and NaCl.

16. A method according to claim 15, the method further comprising the step of resolubilising the fibrinogen precipitate in a buffer comprising NaCl at a concentration of around 100 mM, $CaCl_2$ at a concentration of around 1.1 M, Na-citrate at a concentration of around 10 mM, Tris at a concentration of around 10 mM and sucrose at a concentration of around 45 mM, with a pH of about 6.9.

17. A method according to claim 1, the method further comprising the steps of:
applying the extracted fibrinogen solution to an ion exchange matrix under conditions such that fibrinogen binds to the matrix;
eluting the fibrinogen from the matrix; and
optionally recovering the fibrinogen from the eluate.

18. A method according to claim 17, the method further comprising washing the ion exchange matrix with a buffer comprising at least one ω-amino acid prior to eluting the fibrinogen from the matrix.

19. A method of purifying fibrinogen, the method comprising the steps of:
(a) extracting fibrinogen from a Fraction I precipitate by admixing the Fraction I precipitate with an extraction buffer such that fibrinogen is solubilised in the extraction buffer, wherein the extraction buffer comprises salt at a concentration of at least 0.1 M;
(b) precipitating the fibrinogen; and
(c) solubilising the fibrinogen in a solution comprising at least one ω-amino acid at a concentration of at least 100 mM.

20. A method according to claim 18 wherein the concentration of salt in the extraction buffer is at least 0.4 M.

21. A method according to claim 19 wherein the salt is selected from the group consisting of chloride salts, phosphate salts, acetate salts and a combination thereof.

22. A method according to claim 19 wherein the salt is NaCl.

23. A method according to claim 19 wherein the buffer further comprises Tn-sodium citrate at a concentration of about 20 mM.

24. A method according to claim 19 wherein the extraction buffer further comprises heparin at a concentration of at least 10 IU/ml.

25. A method according to claim 19 wherein the at least one ω-amino acid is present in the extraction buffer at a concentration of at least 5 mM.

26. A method according to claim 19 wherein the extraction buffer comprises Na-citrate at a concentration of about 20 mM, NaCl at a concentration of about 0.8 M and heparin at a concentration of about 60 IU/ml.

27. A method according to claim 19 wherein the fibrinogen is precipitated in step (b) by the addition of a buffer comprising glycine and NaCl.

28. A method according to claim 19 wherein the fibninogen precipitate is solubilised in step (c) using a buffer comprising NaCl at a concentration of around 100 mM, $CaCl_2$ at a concentration of around 1.1 M, Na-citrate at a concentration of around 10 mM, Tris at a concentration of around 10 mM and sucrose at a concentration of around 45 mM.

29. A method according to claim 19, the method further comprising:
(d) applying the fibrinogen solution from step (c) to an ion exchange matrix under conditions such that fibrinogen binds to the matrix;
(e) eluting the fibrinogen from the matrix; and
(f) optionally recovering the fibrinogen from the eluate.

30. A method according to claim 29, the method further comprising washing the ion exchange matrix with a buffer comprising at least one ω-amino acid prior to eluting the fibrinogen from the matrix.

31. A method according to claim 8 wherein the at least one ω-amino acid is ε-amino caproic acid (EACA).

32. A method for purifying fibrinogen, which method comprises the steps of:
(a) extracting fibrinogen from Fraction 1 precipitate by admixing Fraction 1 precipitate with an extraction buffer such that fibrinogen is solubilised in the extraction buffer, wherein the extraction buffer comprises at least one ω-amino acid at a concentration of at least 5 mM;
(b) applying the extraction buffer from step (a) to an ion exchange matrix under conditions such that fibrinogen binds to the matrix;
(c) eluting the fibrinogen from the matrix; and
(d) optionally recovering the fibrinogen from the eluate.

33. A method according to claim 32, the method further comprising washing the ion exchange matrix after step (b) with a solution comprising at least one ω-amino acid.

34. A method of purifying fibrinogen from a fibrinogen containing solution, the method comprising:
(a) applying the solution to an ion exchange matrix, under conditions such that fibrinogen binds to the matrix;
(b) washing the ion exchange matrix with a solution comprising at least one ω-amino acid;
(c) eluting the fibrinogen from the matrix; and
(d) optionally recovering the fibrinogen from the eluate.

35. A method according to claim 32 wherein the ω-amino is ε-amino caproic acid (EACA).

36. A method according to claim 32 wherein the ω-amino acid is present in the extraction buffer at a concentration of between 5–500 mM.

37. A method according to claim 36 wherein the ω-amino acid is present in the extraction buffer at a concentration of between 50–500 mM.

38. A method according to claim 37 wherein the ω-amino acid is present in the extraction buffer at a concentration of about 100 mM.

39. A method according to claim 32 wherein the fibrinogen containing solution is diluted such that the conductivity is below 10.5 mS/cm before it is applied to the ion exchange matrix.

40. A method according to claim 33 wherein the buffer used to wash the ion exchange matrix comprises (i) Tris at a concentration of about 50 mM, (ii) a ω-amino acid at a concentration of about 20 mM, and NaCl at a concentration of about 90 mM.

41. A method according to claim 40 wherein the buffer used to wash the ion exchange matrix has a pH of about 8.0.

42. A method according to claim 40 wherein the buffer used to wash the ion exchange matrix has a conductivity of about 11.1 mS/cm.

43. A method according to claim 40 wherein the fibrinogen is eluted from the matrix in a buffer comprising about 10 mM Tris, 10 mM citrate, 45 mM sucrose; and NaCl at a concentration of between 200 mM to 1.0 M.

44. A method according to claim 43 wherein the NaCl is at a concentration of about 400–500 mM.

45. A method according to claim 43 wherein the elution buffer has a pH of abdut 7.0.

46. A method for purifying fibrinogen, which method comprises:
  (a) extracting fibrinogen from a fibrinogen containing material by admixing the material with an extraction buffer such that fibrinogen is solubilised in the extraction buffer, wherein the extraction buffer comprises at least one ω-amino acid at a concentration of at least 5 mM;
  (b) applying the extraction buffer from step (a) to an ion exchange matrix under conditions such that fibrinogen binds to the matrix;
  (c) washing the ion exchange matrix after step (b) with a solution comprising at least one ω-amino acid;
  (d) eluting the fibrinogen from the matrix; and
  (e) optionally recovering the fibrinogen from the eluate.

* * * * *